United States Patent [19]
Patane et al.

[11] Patent Number: 6,080,760
[45] Date of Patent: Jun. 27, 2000

[54] ALPHA 1A ADRENERGIC RECEPTOR ANTAGONISTS

[75] Inventors: Michael A. Patane, Harleysville; Mark G. Bock, Hatfield, both of Pa.

[73] Assignee: Merck & Co., Inc., Rahway, N.J.

[21] Appl. No.: 09/098,806

[22] Filed: Jun. 17, 1998

Related U.S. Application Data

[60] Provisional application No. 60/050,137, Jun. 18, 1997.

[51] Int. Cl.[7] .................. A61K 31/421; C07D 211/32; C07D 263/26
[52] U.S. Cl. .................. 514/326; 514/369; 514/376; 546/209; 548/188; 548/230
[58] Field of Search .................. 514/326, 369, 514/376; 546/209; 548/188, 230

[56] References Cited

U.S. PATENT DOCUMENTS

| | | | |
|---|---|---|---|
| 4,661,491 | 4/1987 | Regnier | 514/260 |
| 4,769,371 | 9/1988 | Atwal | 544/58.5 |
| 4,847,379 | 7/1989 | Atwal | 544/316 |
| 4,855,301 | 8/1989 | Atwal et al. | 514/269 |
| 5,202,330 | 4/1993 | Atwal et al. | 514/274 |
| 5,574,044 | 11/1996 | Thompson et al. | 514/316 |
| 5,618,827 | 4/1997 | Oxford | 514/326 |

FOREIGN PATENT DOCUMENTS

| | | |
|---|---|---|
| 0 234 830 | 9/1987 | European Pat. Off. . |
| 0 236 902 | 9/1987 | European Pat. Off. . |
| 1329617 | 5/1963 | France . |
| 92/00073 | 1/1992 | WIPO . |
| 92/16213 | 10/1992 | WIPO . |
| 94/08040 | 4/1994 | WIPO . |
| 94/10989 | 5/1994 | WIPO . |
| 94/22829 | 10/1994 | WIPO . |
| 96/14846 | 5/1996 | WIPO . |
| 97/17969 | 5/1997 | WIPO . |
| 97/42956 | 11/1997 | WIPO . |

OTHER PUBLICATIONS

W. C. Wong et al., "Design and Synthesis of Dihydropyrimidines as Alpha 1a Adrenoceptor Selective Antagonists", Abstract No. MEDI 064, 215th ACS National Meeting, Dallas, TX (Mar. 29–Apr. 2, 1998).

B. Lagu et al., "Design, Synthesis and Evaluation of Dihydropyrimidinones as Alpha 1a Selective Antagonists", Abstract No. MEDI 065, 215th ACS National Meeting, Dallas, TX (March 29–Apr. 2, 1998).

D. Nagarathnam et al., "Design, Synthesis and Evaluation of Dihydropyrimidinones as Alpha 1a Selective Antagonists: 6. Synthesis and Structure–Activity Relationship of SNAP 6553 and Analogs", Abstract No. MEDI 066, 215th ACS National Meeting, Dallas, TX (Mar. 29–Apr. 2, 1998).

M. R. Marzabadi et al, "Design, Synthesis and Evaluation of Dihydropyrimidinones and Dihydropyrimidines as Alpha 1a Selective Antagonists: Modification of the Diarylpiperidine Moiety", Abstract No. MEDI 067, 215th ACS National Meeting, Dallas, TX (Mar. 29–Apr. 2, 1998).

Derwent CPI Abstracts No. 90–041498, "Remedy for Dysuria", Abstract of JP01–319418, Nippon Chemifar (1990).

Derwent CPI Abstracts No. 87–027600, "New 1,3–oxazolidin–2–one derivatives", Abstract of JP61–286375, Nippon Chemifar (1987).

G. C. Rovnyak et al., "Dihydropyrimidine Calcium Channel Blockers. 4. Basic 3–Substituted–4–aryl–1,4–dihydropyrimidine–5–carboxylic Acid Esters. Potent Antihypertensive Agents", J. Med. Chem., 35(17), 3254–63 (1992).

K. S. Awal et al., "Dihydropyrimidine Calcium Channel Blockers. 3. 3–Carbamoyl–4–aryl–1,2,3,4–tetrahydro–6–methyl–5–pyrimidinecarboxylic Acid Esters as Orally Effective Antihypertensive Agents", J. Med. Chem., 34(2), 806–11 (1991).

K. S. Atwal et al., "Dihydropyrimidine Calcium Channel Blockers. 2. 3–Substituted–4–aryl–1,4–dihydro–6–methyl–5–pyrimidinecarboxylic Acid Esters as Potent Mimics of Dihydropyridines", J. Med. Chem., 33(9), 2629–35 (1990).

K. S. Atwal et al., "Substituted 1,4–Dihydropyrimidines. 3. Synthesis of Selectively Functionalized 2–Hetero–1,4–dihydropyrimidines", J. Org. Chem., 54(25), 5898–907 (1989).

*Primary Examiner*—Mukund J. Shah
*Assistant Examiner*—Deepak R. Rao
*Attorney, Agent, or Firm*—Kenneth R. Walton; Melvin Winokur

[57] ABSTRACT

This invention relates to certain novel compounds and derivatives thereof, their synthesis, and their use as alpha 1a adrenergic receptor antagonists. One application of these compounds is in the treatment of benign prostatic hyperplasia. These compounds are selective in their ability to relax smooth muscle tissue enriched in the alpha 1a receptor subtype without at the same time inducing hypotension. One such tissue is found surrounding the urethral lining. Therefore, one utility of the instant compounds is to provide acute relief to males suffering from benign prostatic hyperplasia, by permitting less hindered urine flow. Another utility of the instant compounds is provided by combination with a human 5-alpha reductase inhibitory compound, such that both acute and chronic relief from the effects of benign prostatic hyperplasia are achieved.

25 Claims, No Drawings

ALPHA 1A ADRENERGIC RECEPTOR ANTAGONISTS

This application claims the benefit of U.S. Provisional Application No. 60/050,137, filed Jun. 18, 1997.

FIELD OF THE INVENTION

This invention relates to certain novel compounds and derivatives thereof, their synthesis, and their use as alpha 1a adrenoceptor antagonists. More particularly, the compounds of the present invention are useful for treating benign prostatic hyperplasia (BPH).

BACKGROUND OF THE INVENTION

Human adrenergic receptors are integral membrane proteins which have been classified into two broad classes, the alpha and the beta adrenergic receptors. Both types mediate the action of the peripheral sympathetic nervous system upon binding of catecholamines, norepinephrine and epinephrine.

Norepinephrine is produced by adrenergic nerve endings, while epinephrine is produced by the adrenal medulla. The binding affinity of adrenergic receptors for these compounds forms one basis of the classification: alpha receptors bind norepinephrine more strongly than epinephrine and much more strongly than the synthetic compound isoproterenol. The binding affinity of these hormones is reversed for the beta receptors. In many tissues, the functional responses, such as smooth muscle contraction, induced by alpha receptor activation are opposed to responses induced by beta receptor binding.

Subsequently, the functional distinction between alpha and beta receptors was further highlighted and refined by the pharmacological characterization of these receptors from various animal and tissue sources. As a result, alpha and beta adrenergic receptors were further subdivided into alpha 1, alpha 2, $\beta_1$, and $\beta_2$ subtypes. Functional differences between alpha 1 and alpha 2 receptors have been recognized, and compounds which exhibit selective binding between these two subtypes have been developed.

For a general background on the alpha adrenergic receptors, the reader's attention is directed to Robert R. Ruffolo, Jr., *a-Adrenoreceptors: Molecular Biology, Biochemistry and Pharmacology*, (*Progress in Basic and Clinical Pharmacology* series, Karger, 1991), wherein the basis of alpha 1/alpha 2 subclassification, the molecular biology, signal transduction (G-protein interaction and location of the significant site for this and ligand binding activity away from the 3'-terminus of alpha adrenergic receptors), agonist structure-activity relationships, receptor functions, and therapeutic applications for compounds exhibiting alpha-adrenergic receptor affinity was explored.

The cloning, sequencing and expression of alpha receptor subtypes from animal tissues has led to the subclassification of the alpha 1 receptors into alpha 1d (formerly known as alpha 1a or 1a/1d), alpha 1b and alpha 1a (formerly known as alpha 1c) subtypes. Each alpha 1 receptor subtype exhibits its own pharmacologic and tissue specificities. The designation "alpha 1a" is the appellation recently approved by the IUPHAR Nomenclature Committee for the previously designated "alpha 1c" cloned subtype as outlined in the 1995 Receptor and Ion Channel Nomenclature Supplement (Watson and Girdlestone, 1995). The designation alpha 1a is used throughout this application to refer to this subtype. At the same time, the receptor formerly designated alpha 1a was renamed alpha 1d. The new nomenclature is used throughout this application. Stable cell lines expressing these alpha 1 receptor subtypes are referred to herein; however, these cell lines were deposited with the American Type Culture Collection (ATCC) under the old nomenclature. For a review of the classification of alpha 1 adrenoceptor subtypes, see, Martin C. Michel, et al., *Naunyn-Schmiedeberg's Arch. Pharmacol.* (1995) 352:1–10.

The differences in the alpha adrenergic receptor subtypes have relevance in pathophysiologic conditions. Benign prostatic hyperplasia, also known as benign prostatic hypertrophy or BPH, is an illness typically affecting men over fifty years of age, increasing in severity with increasing age. The symptoms of the condition include, but are not limited to, increased difficulty in urination and sexual dysfunction. These symptoms are induced by enlargement, or hyperplasia, of the prostate gland. As the prostate increases in size, it impinges on free-flow of fluids through the male urethra. Concommitantly, the increased noradrenergic innervation of the enlarged prostate leads to an increased adrenergic tone of the bladder neck and urethra, further restricting the flow of urine through the urethra.

In benign prostatic hyperplasia, the male hormone 5alpha-dihydrotestosterone has been identified as the principal culprit. The continual production of 5a-dihydrotestosterone by the male testes induces incremental growth of the prostate gland throughout the life of the male. Beyond the age of about fifty years, in many men, this enlarged gland begins to obstruct the urethra with the pathologic symptoms noted above.

The elucidation of the mechanism summarized above has resulted in the recent development of effective agents to control, and in many cases reverse, the pernicious advance of BPH. In the forefront of these agents is Merck & Co., Inc.s' product PROSCAR® (finasteride). The effect of this compound is to inhibit the enzyme testosterone 5-a reductase, which converts testosterone into 5a-dihydrotesterone, resulting in a reduced rate of prostatic enlargement, and often reduction in prostatic mass.

The development of such agents as PROSCAR® bodes well for the long-term control of BPH. However, as may be appreciated from the lengthy development of the syndrome, its reversal also is not immediate. In the interim, those males suffering with BPH continue to suffer, and may in fact lose hope that the agents are working sufficiently rapidly.

In response to this problem, one solution is to identify pharmaceutically active compounds which complement slower-acting therapeutics by providing acute relief. Agents which induce relaxation of the lower urinary tract tissue, by binding to alpha 1 adrenergic receptors, thus reducing the increased adrenergic tone due to the disease, would be good candidates for this activity. Thus, one such agent is alfuzosin, which is reported in EP 0 204597 to induce urination in cases of prostatic hyperplasia. Likewise, in WO 92/0073, the selective ability of the R(+) enantiomer of terazosin to bind to adrenergic receptors of the alpha1 subtype was reported. In addition, in WO 92/161213, combinations of 5a-reductase inhibitory compounds and alpha1-adrenergic receptor blockers (terazosin, doxazosin, prazosin, bunazosin, indoramin, alfuzosin) were disclosed. However, no information as to the alpha 1d, alpha 1b, or alpha 1a subtype specificity of these compounds was provided as this data and its relevancy to the treatment of BPH was not known. Current therapy for BPH uses existing non-selective alpha 1 antagonists such as prazosin (Minipress, Pfizer), Terazosin (Hytrin, Abbott) or doxazosin mesylate (Cardura, Pfizer). These non-selective antagonists suffer from side effects related to antagonism of the alpha 1d and alpha 1b receptors in the peripheral vasculature, e.g., hypotension and syncope.

The recent cloning of the human alpha 1a adrenergic receptor (ATCC CRL 11140) and the use of a screening assay utilizing the cloned human alpha 1a receptor enables identification of compounds which specifically interact with the human alpha 1a adrenergic receptor. [PCT International Application Publication Nos. WO94/08040, published Apr. 14, 1994 and WO94/10989, published May 26, 1994] As disclosed in the instant patent disclosure, a cloned human alpha 1a adrenergic receptor and a method for identifying compounds which bind the human alpha 1a receptor has now made possible the identification of selective human alpha 1a adrenergic receptor antagonists useful for treating BPH. The instant patent disclosure discloses novel compounds which selectively bind to the human alpha 1a receptor. These compounds are further tested for binding to other human alpha 1 receptor subtypes, as well as counter-screened against other types of receptors (e.g., alpha 2), thus defining the specificity of the compounds of the present invention for the human alpha 1a adrenergic receptor.

It is an object of the present invention to identify compounds which bind to the alpha 1a adrenergic receptor. It is a further object of the invention to identify compounds which act as antagonists of the alpha 1a adrenergic receptor. It is another object of the invention to identify alpha 1a adrenergic receptor antagonist compounds which are useful agents for treating BPH in animals, preferably mammals, especially humans. Still another object of the invention is to identify alpha 1a adrenergic receptor antagonists which are useful for relaxing lower urinary tract tissue in animals, preferably mammals, especially humans.

It has now been found that the compounds of the present invention are alpha 1a adrenergic receptor antagonists. Thus, the compounds of the present invention are useful for treating BPH in mammals. Additionally, it has been found that the alpha 1a adrenergic receptor antagonists of the present invention are also useful for relaxing lower urinary tract tissue in mammals.

SUMMARY OF THE INVENTION

The present invention provides compounds for the treatment of urinary obstruction caused by benign prostatic hyperplasia (BPH). The compounds antagonize the human alpha 1a adrenergic receptor at nanomolar and subnanomolar concentrations while exhibiting at least ten fold lower affinity for the alpha 1d and alpha 1b human adrenergic receptors and many other G-protein coupled receptors. This invention has the advantage over non-selective alpha 1 adrenoceptor antagonists of reduced side effects related to peripheral adrenergic blockade. Such side effects include hypotension, syncope, lethargy, etc. The compounds of the present invention have the structure:

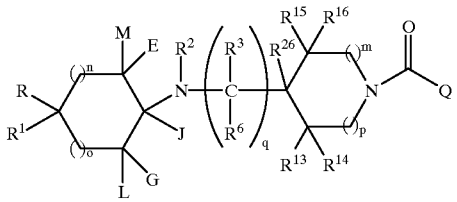

wherein Q is selected from

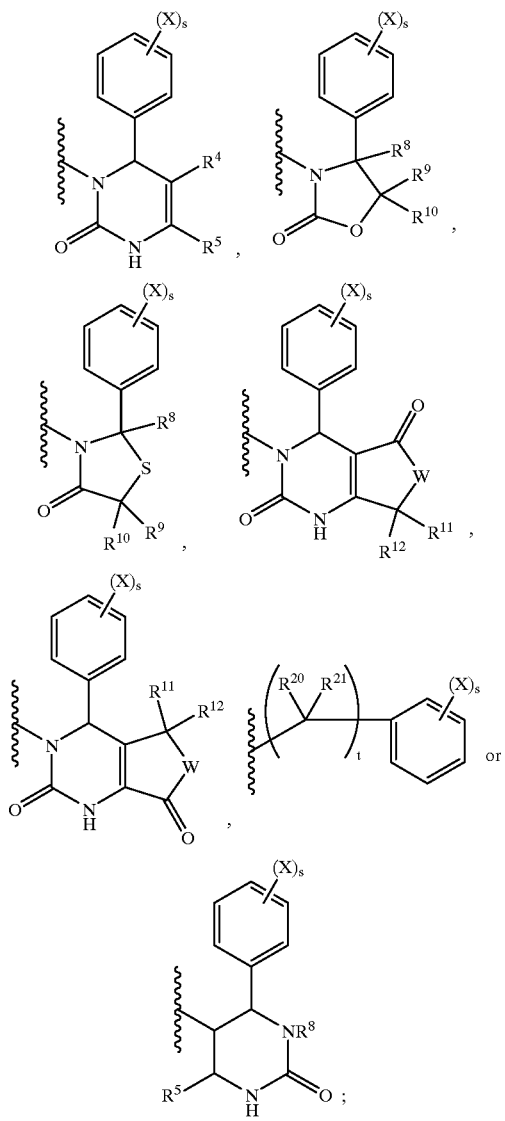

$R^1$ is selected from unsubstituted, mono- or poly-substituted phenyl wherein the substituents on the phenyl are independently selected from halogen, $CF_3$, cyano, nitro, $N(R^{17})_2$, $NR^{17}COR^{18}$, $NR^{17}CON(R^{18})_2$, $NR^{17}SO_2R^7$, $NR^{17}SO_2N(R^{18})_2$, $OR^7$, $(CH_2)_{0-4}CO_2R^{17}$, $(CH_2)_{0-4}CON(R^{17})_2$, $(CH_2)_{0-4}SO_2N(R^{17})_2$, $(CH_2)_{0-4}SO_2R^7$ or $C_{1-4}$ alkyl; or unsubstituted, mono- or poly-substituted pyridyl, pyrazinyl, thienyl, thiazolyl, furanyl, quinazolinyl or naphthyl wherein the substituents on the pyridyl, pyrazinyl, thienyl, thiazolyl, furanyl, quinazolinyl or naphthyl are independently selected from $CF_3$, cyano, nitro, $N(R^{17})_2$, $(CH_2)_{0-4}CO_2R^{17}$, $(CH_2)_{0-4}CON(R^{17})_2$, $(CH_2)_{0-4}SO_2N(R^7)_2$, $(CH_2)_{0-4}SO_2R^7$, phenyl, $OR^7$, halogen, $C_{1-4}$ alkyl or $C_{3-8}$ cycloalkyl;

R is selected from hydrogen, cyano, $OR^7$, $CO_2R^{17}$, $CON(R^{17})_2$, $SO_2R^7$, $SO_2N(R^{17})_2$, tetrazole, isooxadiazole, unsubstituted, mono- or poly-substituted phenyl wherein the substituents on the phenyl are independently selected from halogen, cyano, nitro, $OR^7$, $(CH_2)_{0-4}CO_2R^{17}$, $(CH_2)_{0-4}CON(R^{17})_2$, $N(R^{17})_2$, $NR^{17}COR^7$, $NR^{17}CON(R^{18})_2$, $NR^{17}SO_2R^7$, $NR^{17}SO_2N(R^{18})_2$, $(CH_2)_{0-4}SO_2N(R^{17})_2$, $(CH_2)_{0-4}SO_2R^7$ or $C_{1-4}$ alkyl; or unsubstituted, mono- or poly-substituted pyridyl, thienyl, furanyl or naphthyl wherein the substituents on the pyridyl, thienyl, furanyl or naphthyl are independently selected from $CF_3$, $(CH_2)_{0-4}CO_2R^7$, $(CH_2)_{0-4}CON(R^{17})_2$, $(CH_2)_{0-4}SO_2N(R^{17})_2$, $(CH_2)_{0-4}SO_2R^{17}$, halogen, $C_{1-4}$ alkyl or $C_{3-8}$ cycloalkyl;

E, G, L and M are each independently selected from hydrogen, $C_{1-8}$ alkyl, $C_{3-8}$ cycloalkyl, $(CH_2)_{0-4}OR^7$, $(CH_2)_{0-4}N(R^{17})_2$, $(CH_2)_{0-4}CN$, $(CH_2)_{0-4}CF_3$, $(CH_2)_{0-4}CO_2R^7$, $(CH_2)_{0-4}CON(R^{17})_2$; $(CH_2)_{0-4}SO_2R^{17}$ or $(CH_2)_{0-4}SO_2N(R^{17})_2$;

J is selected from hydrogen, $C_{1-8}$ alkyl, $C_{3-8}$ cycloalkyl, $(CH_2)_{1-4}OR^7$, $(CH_2)_{1-4}N(R^{17})_2$, $(CH_2)_{1-4}CN$, $(CH_2)_{0-4}CF_3$, $(CH_2)_{0-4}CO_2R^7$, $(CH_2)_{0-4}CON(R^{17})_2$, $(CH_2)_{0-4}SO_2R^{17}$ or $(CH_2)_{0-4}SO_2N(R^{17})_2$;

$R^2$, $R^3$ and $R^6$ are each independently selected from hydrogen, $C_{1-8}$ alkyl, $C_{4-8}$ cycloalkyl, $(CH_2)_{0-4}CO_2R^7$, $(CH_2)_{0-4}CON(R^{17})_2$, $(CH_2)_{0-4}COR^7$, $(CH_2)_{2-4}OR^7$, $(CH_2)_{1-4}CF_3$, $(CH_2)_{1-4}SO_2R^7$, $(CH_2)_{0-4}SO_2N(R^{17})_2$ or $(CH_2)_{1-4}CN$;

$R^4$ is selected from hydrogen, $COR^7$, $(CH_2)_{0-4}CN$, $(CH_2)_{0-4}CF_3$, $(CH_2)_{0-4}CO_2R^{17}$, $(CH_2)_{0-4}CON(R^{17})_2$, $(CH_2)_{0-4}SO_2R^7$ or $(CH_2)_{0-4}SO_2N(R^{17})_2$;

$R^5$ is selected from hydrogen, $C_{1-8}$ alkyl, $C_{3-8}$ cycloalkyl, $(CH_2)_{1-4}OR^7$ or $(CH_2)_{0-4}CF_3$;

$R^7$ is selected from hydrogen, $C_{1-8}$ alkyl, $C_{3-8}$ cycloalkyl or $(CH_2)_{0-4}CF_3$;

$R^8$, $R^9$, $R^{10}$, $R^{14}$, $R^{15}$ and $R^{16}$ are each independently selected from hydrogen, $C_{1-8}$ alkyl, $C_{3-8}$ cycloalkyl, $(CH_2)_{2-4}OR^7$ or $(CH_2)_{0-4}CF_3$;

$R^{11}$ and $R^{12}$ are each independently selected from hydrogen, $C_{1-8}$ alkyl or $C_{3-8}$ cycloalkyl;

$R^{13}$ is selected from hydrogen, $C_{1-8}$ alkyl, $C_{3-8}$ cycloalkyl, $(CH_2)_{2-4}OR^7$, $OR^7$ or $(CH_2)_{0-4}CF_3$;

$R^{17}$ and $R^{18}$ are each independently selected from is selected from hydrogen, $C_{1-8}$ alkyl, $C_{3-8}$ cycloalkyl or $(CH_2)_{1-4}CF_3$;

$R^{20}$ is selected from hydrogen, $C_{1-8}$ alkyl, $C_{3-8}$ cycloalkyl, $(CH_2)_{1-4}OR^7$, $(CH_2)_{0-4}CF_3$, unsubstituted, mono- or poly-substituted phenyl wherein the substituents on the phenyl are independently selected from halogen, $CF_3$, cyano, nitro, $OR^7$, $(CH_2)_{0-4}CON(R^{17})_2$, $(CH_2)_{0-4}CO_2R^{17}$ or $C_{1-4}$ alkyl; or unsubstituted, mono- or poly-substituted: pyridyl, pyrazinyl, thienyl, furanyl or naphthyl wherein the substituents on the pyridyl, pyrazinyl, thienyl, furanyl or naphthyl are independently selected from $CF_3$, phenyl, $OR^7$, halogen, $C_{1-4}$ alkyl or $C_{3-8}$ cycloalkyl;

$R^{21}$ is selected from hydrogen, $C_{1-8}$ alkyl, $C_{3-8}$ cycloalkyl, $(CH_2)_{0-4}OR^7$ or $(CH_2)_{0-4}CF_3$;

$R^{26}$ is selected from hydrogen or $OR^{28}$;

$R^{28}$ is selected from hydrogen, $C_{1-8}$ alkyl, $C_{3-8}$ cycloalkyl, $(CH_2)_{0-4}OR^7$ or $(CH_2)_{0-4}CF_3$;

W is O or $NR^{11}$;

each X is independently selected from halogen, cyano, nitro, $C_{1-8}$ alkyl, $C_{3-8}$ cycloalkyl, $(CH_2)_{0-4}OR^7$ or $(CH_2)_{0-4}CF_3$ m, p and q are each independently an integer of from zero to two, provided that when q is zero, $R^{26}$ is hydrogen;

n, o, s and t are each independently an integer of from zero to four;

and the pharmaceutically acceptable salts thereof.

In a first embodiment of the invention is the compound having the structure

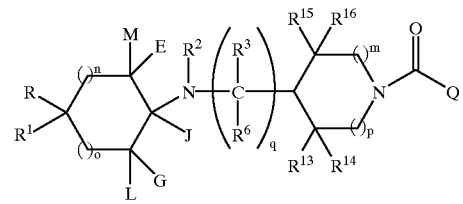

wherein $R^4$ is selected from $COR^7$, $(CH_2)_{0-4}CN$, $(CH_2)_{0-4}CF_3$, $(CH_2)_{0-4}CO_2R^{17}$, $(CH_2)_{0-4}CON(R^{17})_2$, $(CH_2)_{0-4}SO_2R^7$ or $(CH_2)_{0-4}SO_2N(R^{17})_2$;

$R^{13}$ is selected from hydrogen, $C_{1-8}$ alkyl, $C_{3-8}$ cycloalkyl, $(CH_2)_{2-4}OR^7$ or $(CH_2)_{0-4}CF_3$;

and all other variables are as defined above;

and the pharmaceutically acceptable salts thereof.

In a second embodiment of the present invention is the compound of the formula:

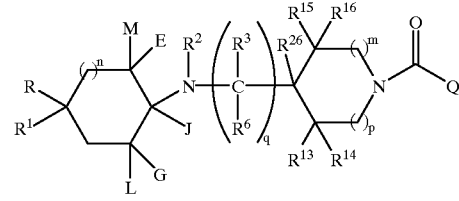

wherein
Q is selected from

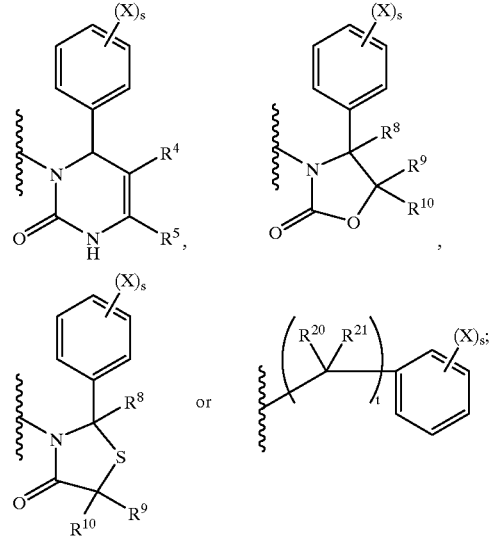

$R^1$ is selected from unsubstituted, mono-, di- or tri-substituted phenyl wherein the substituents on the phenyl are independently selected from halogen, $CF_3$, cyano, nitro, $N(R^{17})_2$, $NR^{17}COR^{18}$, $NR^{17}CON(R^{18})_2$, $NR^{17}SO_2R^7$, $NR^{17}SO_2N(R^{18})_2$, $OR^7$, $(CH_2)_{0-4}CO_2R^{17}$, $(CH_2)_{0-4}CON(R^{17})_2$, $(CH_2)_{0-4}SO_2N(R^{17})_2$, $(CH_2)_{0-4}SO_2R^7$ or $C_{1-4}$ alkyl; or unsubstituted, mono-, di- or tri-substituted pyridyl, pyrazinyl, thienyl, thiazolyl, furanyl, quinazolinyl or naphthyl wherein the substituents on the pyridyl, pyrazinyl, thienyl, thiazolyl, furanyl, quinazolinyl or naphthyl are independently selected from $CF_3$, cyano, nitro, amino, $(CH_2)_{0-4}CO_2R^{17}$, $(CH_2)_{0-4}CON(R^{17})_2$, $(CH_2)_{0-4}SO_2N(R^7)_2$, $(CH_2)_{0-4}SO_2R^7$, phenyl, $OR^7$, halogen, $C_{1-4}$ alkyl or $C_{3-8}$ cycloalkyl;

R is selected from hydrogen, cyano, $OR^7$, $CO_2R^{17}$, $CON(R^{17})_2$, $SO_2R^7$, $SO_2N(R^{17})_2$, tetrazole, isooxadiazole, unsubstituted, mono- or di-substituted phenyl wherein the substituents on the phenyl are independently selected from halogen, cyano, nitro, $OR^7$, $(CH_2)_{0-4}CO_2R^{17}$, $(CH_2)_{0-4}CON(R^{17})_2$, $N(R^{17})_2$, $NR^{17}COR^7$, $NR^{17}CON(R^{18})_2$, $NR^{17}SO_2R^7$, $NR^{17}SO_2N(R^{18})_2$, $(CH_2)_{0-4}SO_2N(R^{17})_2$, $(CH_2)_{0-4}SO_2R^7$ or $C_{1-4}$ alkyl;

E, G, L, M and J are each independently selected from hydrogen, $C_{1-8}$ alkyl, $C_{3-8}$ cycloalkyl or $(CH_2)_{0-4}CF_3$;

$R^2$, $R^3$ and $R^6$ are each independently selected from hydrogen, C1-6 alkyl, $C_{4-6}$ cycloalkyl, $(CH_2)_{0-4}CO_2R^7$, $(CH_2)_{0-4}CON(R^{17})_2$, $(CH_2)_{0-4}COR^7$, $(CH_2)_{2-4}OR^7$, $(CH_2)_{1-4}CF_3$, $(CH_2)_{1-4}SO_2R^7$, $(CH_2)_{0-4}SO_2N(R^{17})_2$ or $(CH_2)_{1-4}CN$;

$R^8$, $R^9$, $R^{10}$, $R^{14}$, $R^{15}$ and $R^{16}$ are each independently selected from hydrogen, $C_{1-6}$ alkyl, $C_{3-6}$ cycloalkyl, $(CH_2)_{2-4}OR^7$ or $(CH_2)_{0-4}CF_3$;

$R^{13}$ is selected from hydrogen, $C_{1-6}$ alkyl, $C_{3-6}$ cycloalkyl, $(CH_2)_{2-4}OR^7$, $OR^7$ or $(CH_2)_{0-4}CF_3$;

$R^{20}$ is selected from hydrogen, $C_{1-8}$ alkyl, $C_{3-8}$ cycloalkyl, $(CH_2)_{1-4}OR^7$, $(CH_2)_{0-4}CF_3$, unsubstituted, mono-, di- or tri-substituted phenyl wherein the substituents on the phenyl are independently selected from halogen, $CF_3$, cyano, nitro, $OR^7$, $(CH_2)_{0-4}CON(R^{17})_2$, $(CH_2)_{0-4}CO_2R^{17}$ or $C_{1-4}$ alkyl; or unsubstituted, mono-, di- or tri-substituted: pyridyl, pyrazinyl, thienyl, furanyl or naphthyl wherein the substituents on the pyridyl, pyrazinyl, thienyl, furanyl or naphthyl are independently selected from $CF_3$, cyano, nitro, amino, phenyl, $OR^7$, halogen, $C_{1-4}$ alkyl or $C_{3-8}$ cycloalkyl;

$R^{21}$ is selected from hydrogen, $C_{1-6}$ alkyl, $C_{3-6}$ cycloalkyl, $(CH_2)_{0-4}OR^7$ or $(CH_2)_{0-4}CF_3$;

$R^{28}$ is selected from hydrogen, $C_{1-6}$ alkyl, $C_{3-6}$ cycloalkyl, $(CH_2)_{2-4}OR^7$ or $(CH_2)_{0-4}CF_3$;

m, n, q and t are each independently an integer from zero to two, provided that when q is zero, $R^{26}$ is hydrogen; and p1 is an integer from zero to one;

and all other variables are as originally defined above;

and the pharmaceutically acceptable salts thereof.

In a third embodiment of the invention is the compound of the formula

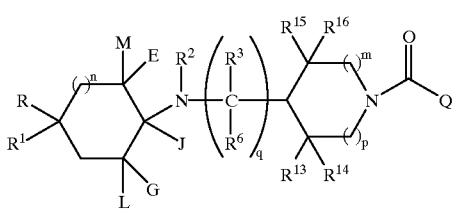

wherein Q is selected from

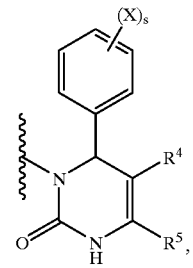 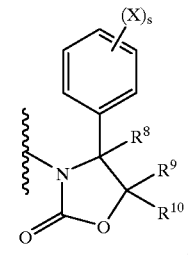

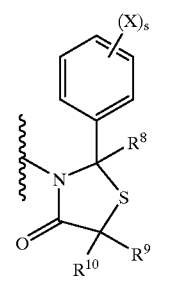 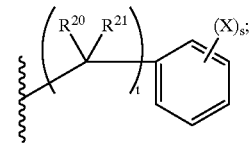

$R^1$ is selected from unsubstituted, mono-, di- or tri-substituted phenyl wherein the substituents on the phenyl are independently selected from halogen, $CF_3$, cyano, nitro, $N(R^{17})_2$, $NR^{17}COR^{18}$, $NR^{17}CON(R^{18})_2$, $NR^{17}SO_2R^7$, $NR^{17}SO_2N(R^{18})_2$, $OR^7$, $(CH_2)_{0-4}CO_2R^{17}$, $(CH_2)_{0-4}CON(R^{17})_2$, $(CH_2)_{0-4}SO_2N(R^{17})_2$, $(CH_2)_{0-4}SO_2R^7$ or $C_{1-4}$ alkyl; or unsubstituted, mono-, di- or tri-substituted pyridyl, pyrazinyl, thienyl, thiazolyl, furanyl, quinazolinyl or naphthyl wherein the substituents on the pyridyl, pyrazinyl, thienyl, thiazolyl, furanyl, quinazolinyl or naphthyl are independently selected from $CF_3$, cyano, nitro, amino, $(CH_2)_{0-4}CO_2R^{17}$, $(CH_2)_{0-4}CON(R^{17})_2$, $(CH_2)_{0-4}SO_2N(R^7)_2$, $(CH_2)_{0-4}SO_2R^7$, phenyl, $OR^7$, halogen, $C_{1-4}$ alkyl or $C_{3-8}$ cycloalkyl;

R is selected from hydrogen, cyano, $OR^7$, $CO_2R^{17}$, $CON(R^{17})_2$, $SO_2R^7$, $SO_2N(R^{17})_2$, tetrazole, isooxadiazole, unsubstituted, mono- or di-substituted phenyl wherein the substituents on the phenyl are independently selected from halogen, cyano, nitro, $OR^7$, $(CH_2)_{0-4}CO_2R^{17}$, $(CH_2)_{0-4}CON(R^{17})_2$, $N(R^{17})_2$, $NR^{17}COR^7$, $NR^{17}CON(R^{18})_2$, $NR^{17}SO_2R^7$, $NR^{17}SO_2N(R^{18})_2$, $(CH_2)_{0-4}SO_2N(R^{17})_2$, $(CH_2)_{0-4}SO_2R^7$ or $C_{1-4}$ alkyl;

E, G, L, M and J are each independently selected from hydrogen, $C_{1-8}$ alkyl, $C_{3-8}$ cycloalkyl or $(CH_2)_{0-4}CF_3$;

$R^2$, $R^3$ and $R^6$ are each independently selected from hydrogen, $C_{1-6}$ alkyl, $C_{4-6}$ cycloalkyl, $(CH_2)_{0-4}CO_2R^7$, $(CH_2)_{0-4}CON(R^{17})_2$, $(CH_2)_{0-4}COR^7$, $(CH_2)_{2-4}OR^7$, $(CH_2)_{1-4}CF_3$, $(CH_2)_{1-4}SO_2R^7$, $(CH_2)_{0-4}SO_2N(R^{17})_2$ or $(CH_2)_{1-4}CN$;

$R^8$, $R^9$, $R^{10}$, $R^{13}$, $R^{14}$, $R^{15}$ and $R^{16}$ are each independently selected from hydrogen, $C_{1-6}$ alkyl, $C_{3-6}$ cycloalkyl, $(CH_2)_{2-4}OR^7$ or $(CH_2)_{0-4}CF_3$;

$R^{20}$ is selected from hydrogen, $C_{1-8}$ alkyl, $C_{3-8}$ cycloalkyl, $(CH_2)_{1-4}OR^7$, $(CH_2)_{0-4}CF_3$, unsubstituted, mono-, di- or tri-substituted phenyl wherein the substituents on the phenyl are independently selected from halogen, $CF_3$, cyano, nitro, $OR^7$, $(CH_2)_{0-4}CON(R^{17})_2$, $(CH_2)_{0-4}CO_2R^{17}$ or $C_{1-4}$ alkyl; or unsubstituted, mono-, di- or tri-substituted: pyridyl, pyrazinyl, thienyl, furanyl or naphthyl wherein the substituents on the pyridyl, pyrazinyl, thienyl, furanyl or naphthyl are independently selected from $CF_3$, cyano, nitro, amino, phenyl, $OR^7$, halogen, $C_{1-4}$ alkyl or $C_{3-8}$ cycloalkyl;

$R^{21}$ is selected from hydrogen, $C_{1-6}$ alkyl, $C_{3-6}$ cycloalkyl, $(CH_2)_{0-4}OR^7$ or $(CH_2)_{0-4}CF_3$;

m, n, q and t are each independently an integer from zero to two;

p is an integer from zero to one;

and all other variables are as defined previously in the first embodiment;

and the pharmaceutically acceptable salts thereof.

In a first class of the invention is the compound of the formula

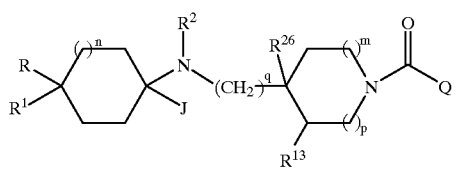

wherein Q is selected from

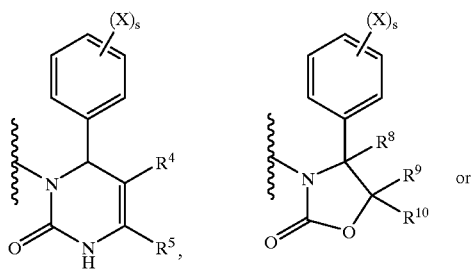

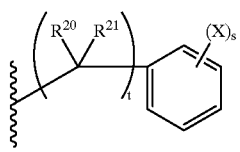

$R^2$ is selected from hydrogen, $C_{1-6}$ alkyl, $C_{4-6}$ cycloalkyl or $(CH_2)_{1-4}CF_3$;

$R^4$ is selected from hydrogen, $COR^7$, $(CH_2)_{0-2}CO_2R^7$, $SO_2R^7$ or $(CH_2)_{0-2}CON(R^{17})_2$;

$R^5$ is selected from hydrogen, $C_{1-6}$ alkyl, $C_{3-6}$ cycloalkyl, $(CH_2)_{1-3}OR^7$ or $(CH_2)_{0-3}CF_3$; and $R^7$ is selected from hydrogen, $C_{1-6}$ alkyl, $C_{3-6}$ cycloalkyl or $(CH_2)_{0-3}CF_3$;

$R^{13}$ is hydrogen or $OR^7$;

$R^{17}$ and $R^{18}$ are each independently selected from is selected from hydrogen, $C_{1-6}$ alkyl, $C_{3-6}$ cycloalkyl or $(CH_2)_{1-4}CF_3$;

$R^{20}$ is selected from hydrogen, $C_{1-6}$ alkyl, $C_{3-6}$ cycloalkyl, $(CH_2)_{2-4}OR^7$, $(CH_2)_{0-2}CF_3$ or unsubstituted, mono- or di-substituted phenyl wherein the substituents on the phenyl are independently selected from halogen, $CF_3$, cyano, nitro, amino, $OR^7$, $CO_2R^{17}$, $CON(R^{17})_2$ or $C_{1-4}$ alkyl;

$R^{26}$ is hydrogen or $OR^{28}$, wherein $R^{28}$ is hydrogen or $C_{1-6}$ alkyl;

and all other variables are as defined above in the second embodiment;

and the pharmaceutically acceptable salts thereof.

In a second class of the invention is the compound of the formula

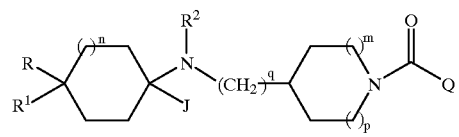

wherein Q is selected from

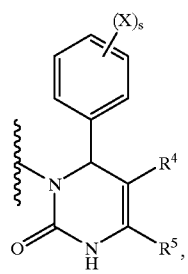 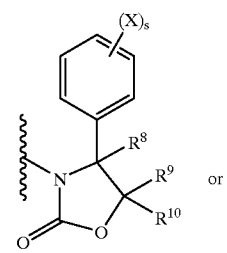 or

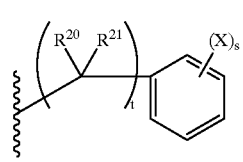

$R^2$ is selected from hydrogen, $C_{1-6}$ alkyl, $C_{4-6}$ cycloalkyl or $(CH_2)_{1-4}CF_3$;

$R^4$ is selected from $COR^7$, $(CH_2)_{0-2}CO_2R^{17}$, $SO_2R^7$ or $(CH_2)_{0-2}CON(R^{17})_2$;

$R^5$ is selected from hydrogen, $C_{1-6}$ alkyl, $C_{3-6}$ cycloalkyl, $(CH_2)_{1-3}OR^7$ or $(CH_2)_{0-3}CF_3$; and $R^7$ is selected from hydrogen, $C_{1-6}$ alkyl, $C_{3-6}$ cycloalkyl or $(CH_2)_{0-3}CF_3$;

$R^{17}$ and $R^{18}$ are each independently selected from is selected from hydrogen, $C_{1-6}$ alkyl, $C_{3-6}$ cycloalkyl or $(CH_2)_{1-4}CF_3$;

$R^{20}$ is selected from hydrogen, $C_{1-6}$ alkyl, $C_{3-6}$ cycloalkyl, $(CH_2)_{2-4}OR^7$, $(CH_2)_{0-2}CF_3$ or unsubstituted, mono- or di-substituted phenyl wherein the substituents on the phenyl are independently selected from halogen, $CF_3$, cyano, nitro, amino, $OR^7$, $CO_2R^{17}$, $CON(R^{17})_2$ or $C_{1-4}$ alkyl;

and all other variables are as defined above in the third embodiment;

and the pharmaceutically acceptable salts thereof.

In a first subclass of the invention is the compound of the formula

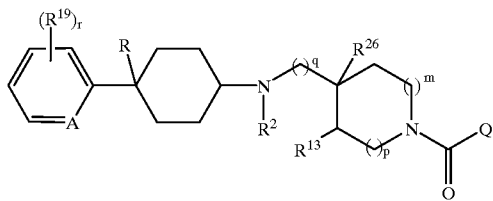

wherein A is C—$R^{19}$ or N;
R is selected from hydrogen, cyano, hydroxy, $CO_2R^{17}$, $CON(R^{17})_2$, $SO_2R^7$, $SO_2N(R^{17})_2$;
$R^2$ is selected from hydrogen or $CH_2CF_3$;
$R^{13}$ is selected from hydrogen or hydroxy;
each $R^{19}$ is independently selected from halogen, $CF_3$, cyano, nitro, amino, $OR^7$, $CO_2R^{17}$, $CON(R^{17})_2$ or $C_{1-4}$ alkyl;
$R^{20}$ is selected from hydrogen, $C_{1-4}$ alkyl or unsubstituted, mono- or di-substituted phenyl wherein the substituents on the phenyl are independently selected from halogen, $CF_3$, cyano, nitro, amino, $OR^7$, $CO_2R^{17}$, $CON(R^{17})_2$ or $C_{1-4}$ alkyl;
$R^{26}$ is selected from hydrogen or hydroxy;
each X is halogen;
q is an integer from zero to one, provided that when q is zero, $R^{26}$ is hydrogen; and
r is an integer from zero to two;
s is an integer from zero to three;
and all other variables are as defined previously in the first class;
and the pharmaceutically acceptable salts thereof.

In a second subclass of the invention is the compound of the formula

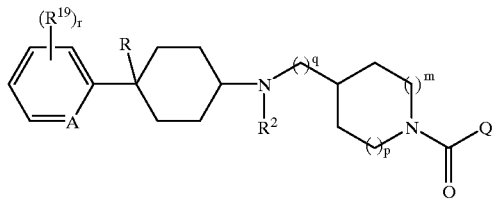

wherein A is C—$R^{19}$ or N;
R is selected from hydrogen, cyano, hydroxy, $CO_2R^{17}$, $CON(R^{17})_2$, $SO_2R^7$, $SO_2N(R^{17})_2$;
$R^2$ is selected from hydrogen or $CH_2CF_3$;
each $R^{19}$ is independently selected from halogen, $CF_3$, cyano, nitro, amino, $OR^7$, $CO_2R^{17}$, $CON(R^{17})_2$ or $C_{1-4}$ alkyl;
$R^{20}$ is selected from hydrogen, $C_{1-4}$ alkyl or unsubstituted, mono- or di-substituted phenyl wherein the substituents on the phenyl are independently selected from halogen, $CF_3$, cyano, nitro, amino, $OR^7$, $CO_2R^{17}$, $CON(R^{17})_2$ or $C_{1-4}$ alkyl;
each X is halogen;
q is an integer from zero to one;
r is an integer from zero to two;
s is an integer from zero to three;
and all other variables are as defined previously in the second class;
and the pharmaceutically acceptable salts thereof.

Illustrative of the invention is the compound selected from

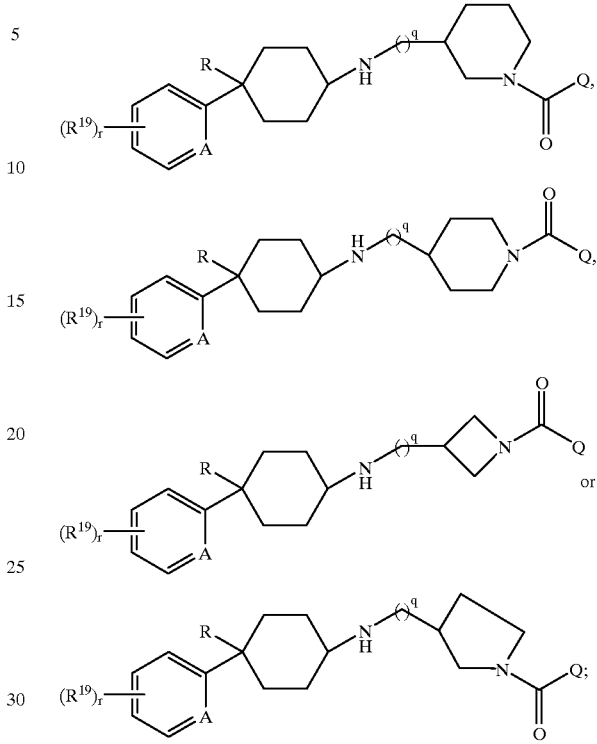

wherein Q is selected from

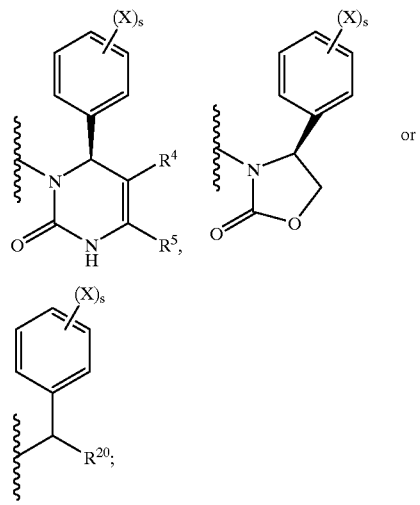

wherein R is selected from hydrogen or cyano;
$R^4$ is selected from $COR^7$, $CO_2R^{17}$ or $CON(R^{17})_2$;
$R^5$ is selected from hydrogen, $C_{1-6}$ alkyl, $C_{3-6}$ cycloalkyl, $(CH_2)_{1-2}OR^7$ or $(CH_2)_2CF_3$;
$R^{19}$ is selected from hydrogen, halogen, $C_{1-6}$ alkyl or $CF_3$;
each X is fluoro; and
and all other variables are as defined previously in the second subclass;
and the pharmaceutically acceptable salts thereof.

An illustration of the invention is a pharmaceutical composition comprising a therapeutically effective amount of any of the compounds described above and a pharmaceutically acceptable carrier. An example of the invention is a pharmaceutical composition made by combining any of the compounds described above and a pharmaceutically acceptable carrier. Another illustration of the invention is a process for making a pharmaceutical composition comprising combining any of the compounds described above and a pharmaceutically acceptable carrier.

Exemplifying the invention is the composition further comprising a therapeutically effective amount of a testosterone 5-alpha reductase inhibitor. Preferably, the testosterone 5-alpha reductase inhibitor is a type 1, a type 2, both a type 1 and a type 2 (i.e., a three component combination comprising any of the compounds described above combined with both a type 1 testosterone 5-alpha reductase inhibitor and a type 2 testosterone 5-alpha reductase inhibitor) or a dual type 1 and type 2 testosterone 5-alpha reductase inhibitor. More preferably, the testosterone 5-alpha reductase inhibitor is a type 2 testosterone 5-alpha reductase inhibitor. Most preferably, the testosterone 5-alpha reductase inhibitor is finasteride.

More specifically illustrating the invention is a method of treating benign prostatic hyperplasia in a subject in need thereof which comprises administering to the subject a therapeutically effective amount of any of the compounds (or any of the compositions) described above.

Further exemplifying the invention is the method of treating BPH wherein the compound (or composition) additionally does not cause a fall in blood pressure at dosages effective to alleviate BPH.

Another example of the invention is the method of treating benign prostatic hyperplasia wherein the compound is administered in combination with a testosterone 5-alpha reductase inhibitor. Preferably, the testosterone 5-alpha reductase inhibitor is finasteride.

Further illustrating the invention is a method of inhibiting contraction of prostate tissue or relaxing lower urinary tract tissue in a subject in need thereof which comprises administering to the subject a therapeutically effective amount of any of the compounds (or any of the compositions) described above.

More specifically exemplifying the invention is the method of inhibiting contraction of prostate tissue or relaxing lower urinary tract tissue wherein the compound (or composition) additionally does not cause a fall in blood pressures at dosages effective to inhibit contraction of prostate tissue.

More particularly illustrating the invention is the method of inhibiting contraction of prostate tissue or relaxing lower urinary tract tissue wherein the compound (or composition) is administered in combination with a testosterone 5-alpha reductase inhibitor; preferably, the testosterone 5-alpha reductase inhibitor is finasteride.

More particularly exemplifying the invention is a method of treating a disease which is susceptible to treatment by antagonism of the alpha 1a receptor which comprises administering to a subject in need thereof an amount of any of the compounds described above effective to treat the disease. Diseases which are susceptible to treatment by antagonism of the alpha 1a receptor include, but are not limited to, BPH, high intraocular pressure, high cholesterol, impotency, sympathetically mediated pain, migraine (see, K. A. Vatz, *Headache* 1997:37: 107–108) and cardiac arrhythmia.

An additional illustration of the invention is the use of any of the compounds described above in the preparation of a medicament for: a) the treatment of benign prostatic hyperplasia; b) relaxing lower urinary tract tissue; or c) inhibiting contraction of prostate tissue; in a subject in need thereof.

An additional example of the invention is the use of any of the alpha 1a antagonist compounds described above and a 5-alpha reductase inhibitor for the manufacture of a medicament for: a) treating benign prostatic hyperplasia; b) relaxing lower urinary tract tissue; or c) inhibiting contraction of prostate tissue which comprises an effective amount of the alpha 1a antagonist compound and an effective amount of 5-alpha reductase inhibitor, together or separately.

DETAILED DESCRIPTION OF THE INVENTION

Representative compounds of the present invention exhibit high selectivity for the human alpha 1a adrenergic receptor. One implication of this selectivity is that these compounds display selectivity for lowering intraurethral pressure without substantially affecting diastolic blood pressure.

Representative compounds of this invention display sub-micromolar affinity for the human alpha 1a adrenergic receptor subtype while displaying at least ten-fold lower affinity for the human alpha 1d and alpha 1b adrenergic receptor subtypes, and many other G-protein coupled human receptors. Particular representative compounds of this invention exhibit nanomolar and subnanomolar affinity for the human alpha 1a adrenergic receptor subtype while displaying at least 30 fold lower affinity for the human alpha 1d and alpha 1b adrenergic receptor subtypes, and many other G-protein coupled human receptors (e.g., serotonin, dopamine, alpha 2 adrenergic, beta adrenergic or muscarinic receptors).

These compounds are administered in dosages effective to antagonize the alpha 1a receptor where such treatment is needed, as in BPH. For use in medicine, the salts of the compounds of this invention refer to non-toxic "pharmaceutically acceptable salts." Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts. Thus, representative pharmaceutically acceptable salts include the following:

Acetate, Benzenesulfonate, Benzoate, Bicarbonate, Bisulfate, Bitartrate, Borate, Bromide, Calcium, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isothionate, Lactate, Lactobionate, Laurate, Malate, Maleate, Mandelate, Mesylate, Methylbromide, Methylnitrate, Methylsulfate, Mucate, Napsylate, Nitrate, N-methylglucamine ammonium salt, Oleate, Pamoate (Embonate), Palmitate, Pantothenate, Phosphate/diphosphate, Polygalacturonate, Salicylate, Stearate, Sulfate, Subacetate, Succinate, Tannate, Tartrate, Teoclate, Tosylate, Triethiodide and Valerate.

Compounds of this invention are used to reduce the acute symptoms of BPH. Thus, compounds of this invention may be used alone or in conjunction with a more long-term anti-BPH therapeutics, such as testosterone 5-a reductase inhibitors, including PROSCAR® (finasteride). Aside from their utility as anti-BPH agents, these compounds may be used to induce highly tissue-specific, localized alpha 1a adrenergic receptor blockade whenever this is desired. Effects of this blockade include reduction of intra-ocular pressure, control of cardiac arrhythmias, and possibly a host of alpha 1a receptor mediated central nervous system events.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

Where the compounds according to the invention have at least one chiral center, they may accordingly exist as enantiomers. Where the compounds according to the invention possess two or more chiral centers, they may additionally exist as diastereoisomers. It is to be understood that all such isomers and mixtures thereof are encompassed within the scope of the present invention. Furthermore, some of the crystalline forms for compounds of the present invention may exist as polymorphs and as such are intended to be included in the present invention. In addition, some of the compounds of the present invention may form solvates with water (i.e., hydrates) or common organic solvents. Such solvates are also encompassed within the scope of this invention.

The term "alkyl" shall mean straight or branched chain alkanes of one to ten total carbon atoms, or any number within this range (i.e., methyl, ethyl, 1-propyl, 2-propyl, n-butyl, s-butyl, t-butyl, etc.).

The term "alkenyl" shall mean straight or branched chain alkenes of two to ten total carbon atoms, or any number within this range.

The term "aryl" as used herein, except where otherwise specifically defined, refers to unsubstituted, mono- or poly-substituted aromatic groups such as phenyl or naphthyl.

The term "cycloalkyl" shall mean cyclic rings of alkanes of three to eight total carbon atoms (i.e., cyclopropyl, cyclobutyl, cyclopentyl, cyclohexyl, cycloheptyl or cyclooctyl).

Whenever the term "alkyl" or "aryl" or either of their prefix roots appear in a name of a substituent (e.g., aralkoxyaryloxy) it shall be interpreted as including those limitations given above for "alkyl" and "aryl." Designated numbers of carbon atoms (e.g., $C_{1-10}$) shall refer independently to the number of carbon atoms in an alkyl or cyclic alkyl moiety or to the alkyl portion of a larger substituent in which alkyl appears as its prefix root.

The term "halogen" shall include iodine, bromine, chlorine and fluorine.

The term "substituted" shall be deemed to include multiple degrees of substitution by a named substituent. The term "poly-substituted" as used herein shall include di-, tri-, tetra- and penta-substitution by a named substituent. Preferably, a poly-substituted moiety is di-, tri- or tetra-substituted by the named substituents, most preferably, di- or tri-substituted.

It is intended that the definition of any substituent or variable (e.g., X, $R^{17}$, $R^{18}$) at a particular location in a molecule be independent of its definitions elsewhere in that molecule. Thus, $-N(R^{17})_2$ represents $-NH_2$, $-NHCH_3$, $-NHC_2H_5$, $-N(CH_3)C_2H_5$, etc. It is understood that substituents and substitution patterns on the compounds of the instant invention can be selected by one of ordinary skill in the art to provide compounds that are chemically stable and that can be readily synthesized by techniques known in the art as well as those methods set forth below.

Where multiple substituent moieties are disclosed or claimed, the substituted compound can be independently substituted by one or more of the disclosed or claimed substituent moieties, singly or plurally.

The term heterocycle or heterocyclic ring, as used herein, represents an unsubstituted or substituted stable 5- to 7-membered monocyclic ring system which may be saturated or unsaturated, and which consists of carbon atoms and from one to three heteroatoms selected from N, O or S, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but is not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, and oxadiazolyl. Morpholino is the same as morpholinyl.

The term "thienyl," as used herein, refers to the group

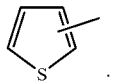

The terms "(+)-DHP" and "DHP" as used herein, refer to a dihydropyrimidinone group of the formula

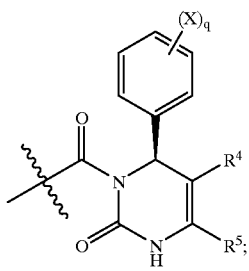

for example:

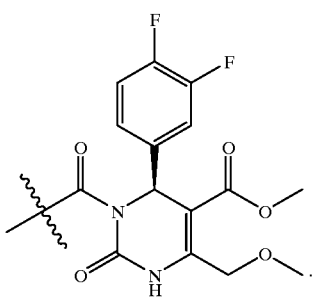

The term "activated (+)-DHP," as used herein, refers to a N-3-(activated)carbamate of the desired dihydropyrimidinone where the activating group is, for example, a p-nitrophenyloxy group. A specific example of an activated (+)-DHP is 4-(3,4-difluorophenyl)- 5-methoxycarbonyl-6-methoxymethyl-2-oxo-1,2,3,4-tetrahydropyrimidine-3-carboxylic acid (4-nitrophenyl ester).

The term "(S)-oxa" as used herein, refers to an oxazolidinone group of the formula

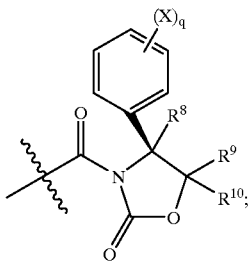

for example,

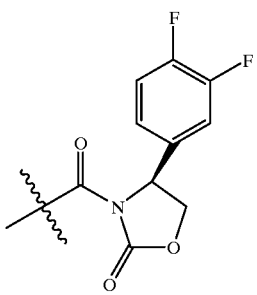

The term "activated (S)-oxa" as used herein, refers to an N-(activated)carbamate of the desired oxazolidinone where the activating group is, for example, a p-nitrophenyloxy group. A specific example of an activated (S)-oxa group is 4-(3,4-difluorophenyl)-2-oxo-oxazolidine-3-carboxylic acid 4-nitrophenyl ester.

The term "selective alpha 1a adrenergic receptor antagonist," as used herein, refers to an alpha 1a antagonist compound which is at least ten fold selective for the human alpha 1a adrenergic receptor as compared to the human alpha 1b, alpha 1d, alpha 2a, alpha 2b and alpha 2c adrenergic receptors.

The term "lower urinary tract tissue," as used herein, refers to and includes, but is not limited to, prostatic smooth muscle, the prostatic capsule, the urethra and the bladder neck.

The term "subject," as used herein refers to an animal, preferably a mammal, most preferably a human, who has been the object of treatment, observation or experiment.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated.

The present invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

As used herein, the term "composition" is intended to encompass a product comprising the specified ingredients in the specified amounts, as well as any product which results, directly or indirectly, from combination of the specified ingredients in the specified amounts.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Where the processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis, John Wiley & Sons*, 1991. The protecting groups may be removed at a convenient subsequent stage using methods known from the art.

The specificity of binding of compounds showing affinity for the alpha 1a receptor is shown by comparing affinity to membranes obtained from tranfected cell lines that express the alpha 1a receptor and membranes from cell lines or tissues known to express other types of alpha (e.g., alpha 1d, alpha 1b) or beta adrenergic receptors. Expression of the cloned human alpha 1d, alpha 1b, and alpha 1a receptors and comparison of their binding properties with known selective antagonists provides a rational way for selection of compounds and discovery of new compounds with predictable pharmacological activities. Antagonism by these compounds of the human alpha 1a adrenergic receptor subtype may be functionally demonstrated in anesthetized animals. These compounds may be used to increase urine flow without exhibiting hypotensive effects.

The ability of compounds of the present invention to specifically bind to the alpha 1a receptor makes them useful for the treatment of BPH. The specificity of binding of compounds showing affinity for the alpha 1a receptor is compared against the binding affinities to other types of alpha or beta adrenergic receptors. The human alpha adrenergic receptor of the 1a subtype was recently identified, cloned and expressed as described in PCT International Application Publication Nos. WO94/08040, published Apr. 14, 1994 and WO 94/21660, published Sep. 29, 1994. The cloned human alpha 1a receptor, when expressed in mammalian cell lines, is used to discover ligands that bind to the receptor and alter its function. Expression of the cloned human alpha 1d, alpha 1b, and alpha 1a receptors and comparison of their binding properties with known selective antagonists provides a rational way for selection of compounds and discovery of new compounds with predictable pharmacological activities.

Compounds of this invention exhibiting human alpha 1a adrenergic receptor antagonism may further be defined by counterscreening. This is accomplished according to methods known in the art using other receptors responsible for mediating diverse biological functions. [See e.g., PCT International Application Publication No. WO94/10989, published May 26, 1994; U.S. Pat. No. 5,403,847, issued Apr. 4, 1995]. Compounds which are both selective amongst the various human alpha1 adrenergic receptor subtypes and which have low affinity for other receptors, such as the alpha2 adrenergic receptors, the β-adrenergic receptors, the muscarinic receptors, the serotonin receptors, and others are particularly preferred. The absence of these non-specific activities may be confirmed by using cloned and expressed receptors in an analogous fashion to the method disclosed herein for identifying compounds which have high affinity for the various human alpha1 adrenergic receptors. Furthermore, functional biological tests are used to confirm the effects of identified compounds as alpha 1a adrenergic receptor antagonists.

The present invention also has the objective of providing suitable topical, oral, systemic and parenteral pharmaceutical formulations for use in the novel methods of treatment of the present invention. The compositions containing compounds of this invention as the active ingredient for use in the specific antagonism of human alpha 1a adrenergic receptors can be administered in a wide variety of therapeutic dosage forms in conventional vehicles for systemic administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as an alpha 1a antagonistic agent.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinyl-pyrrolidone, pyran copolymer, polyhydroxypropylmethacryl-amidephenol, polyhydroxy-ethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

Compounds of this invention may be administered in any of the foregoing compositions and according to dosage regimens established in the art whenever specific blockade of the human alpha 1a adrenergic receptor is required.

The daily dosage of the products may be varied over a wide range from 0.01 to 1,000 mg per adult human per day. For oral administration, the compositions are preferably provided in the form of tablets containing 0.01, 0.05, 0.1, 0.5, 1.0, 2.5, 5.0, 10.0, 15.0, 25.0, 50.0 and 100 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. An effective amount of the drug is ordinarily supplied at a dosage level of from about 0.0002 mg/kg to about 20 mg/kg of body weight per day. Preferably, the range is from about 0.001 to 10 mg/kg of body weight per day, and especially from about 0.001 mg/kg to 7 mg/kg of body weight per day. The compounds may be administered on a regimen of 1 to 4 times per day.

Compounds of this patent disclosure may be used alone at appropriate dosages defined by routine testing in order to obtain optimal antagonism of the human alpha 1a adrenergic receptor while minimizing any potential toxicity. In addition, co-administration or sequential administration of other agents which alleviate the effects of BPH is desirable. Thus, in one embodiment, this includes administration of compounds of this invention and a human testosterone 5-a reductase inhibitor. Included with this embodiment are inhibitors of 5-alpha reductase isoenzyme 2. Many such compounds are now well known in the art and include such compounds as PROSCAR®, (also known as finasteride, a 4-Aza-steroid; see U.S. Pat. Nos. 4,377,584 and 4,760,071, for example). In addition to PROSCAR®, which is principally active in prostatic tissue due to its selectivity for human 5-a reductase isozyme 2, combinations of compounds which are specifically active in inhibiting testosterone 5-alpha reductase isozyme 1 and compounds which act as dual inhibitors of both isozymes 1 and 2, are useful in combination with compounds of this invention. Compounds that are active as 5a-reductase inhibitors have been described in WO93/23420, EP 0572166; WO 93/23050; WO93/23038,; WO93/23048; WO93/23041; WO93/23040; WO93/23039; WO93/23376; WO93/23419, EP 0572165; WO93/23051.

The dosages of the alpha 1a adrenergic receptor and testosterone 5-alpha reductase inhibitors are adjusted when combined to achieve desired effects. As those skilled in the art will appreciate, dosages of the 5-alpha reductase inhibitor and the alpha 1a adrenergic receptor antagonist may be independently optimized and combined to achieve a synergistic result wherein the pathology is reduced more than it would be if either agent were used alone. In accordance with the method of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly.

Thus, in one preferred embodiment of the present invention, a method of treating BPH is provided which comprises administering to a subject in need of treatment any of the compounds of the present invention in combination with finasteride effective to treat BPH. The dosage of finasteride administered to the subject is about 0.01 mg per subject per day to about 50 mg per subject per day in combination with an alpha 1a antagonist. Preferably, the dosage of finasteride in the combination is about 0.2 mg per subject per day to about 10 mg per subject per day, more preferably, about 1 to about 7 mg per subject to day, most preferably, about 5 mg per subject per day.

For the treatment of benign prostatic hyperplasia, compounds of this invention exhibiting alpha 1a adrenergic receptor blockade can be combined with a therapeutically effective amount of a 5a-reductase 2 inhibitor, such as finasteride, in addition to a 5a-reductase 1 inhibitor, such as 4,7β-dimethyl-4-aza-5a-cholestan-3-one, in a single oral, systemic, or parenteral pharmaceutical dosage formulation. Alternatively, a combined therapy can be employed wherein the alpha 1a adrenergic receptor antagonist and the 5a-reductase 1 or 2 inhibitor are administered in separate oral, systemic, or parenteral dosage formulations. See, e.g., U.S. Pat. Nos. 4,377,584 and 4,760,071 which describe dosages and formulations for 5a-reductase inhibitors.

Abbreviations used in the instant specification, particularly the Schemes and Examples, are as follows:
Aq=aqueous
BCE=bromochloroethane Boc or BOC=t-butyloxycarbonyl
$BOC_2O$=di-tert-butyl dicarbonate
BOPCl=bis(2-oxo-3-oxazolidinyl)phosphinic chloride
Cbz=benzyloxycarbonyl
Cbz-Cl=benzyloxycarbonyl chloride
DEAD=diethylazodicarboxylate
DMF=N,N-dimethylformamide
DMSO=dimethylsulfoxide
DPPA=diphenylphosphoryl azide
EDCI=1-(3-dimethylaminopropyl)-3-ethylcarbodiimide hydrochloride
Et=ethyl
$Et_3N$=triethylamine
EtOAc=ethyl acetate
EtOH=ethanol
FABLRMS=fast atom bombardment low resolution mass spectroscopy
HPLC=high performance liquid chromatography
HOAc=acetic acid
HOBt=1-hydroxy benzotriazole hydrate
i-PrOH=2-propanol
i-$Pr_2$NEt=diisopropylethylamine
KOtBu=potassium tert-butoxide
LAH=lithium aluminum hydride
mCPBA=meta-chloroperbenzoic acid
Me=methyl
MeOH=methanol
NMR=nuclear magnetic resonance
$Nu^-$=nucleophile
PCTLC=preparative centrifugal thin layer chromatography
PEI=polyethylenimine
Ph=phenyl
RT=retention time
tBuOH=tert-butanol
TEBAC=benzyltriethylammonium chloride
TFA=trifluoroacetic acid
THF=tetrahydrofuran
TLC=thin layer chromatography
TMS=trimethylsilyl
TMSCN=trimethylsilyl cyanide The compounds of the present invention can be prepared readily according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Unless otherwise indicated, all variables are as defined above.

In general, compounds claimed within this invention are readily accessible from an appropriately substituted cyclic alkanone via reductive amination with a mono blocked diamino equivalent, Scheme 1. Protection of the incipient amino group may be required, followed by deprotection of the terminal amino group. Acylation or alkylation provides the desired analog. An example of this strategy is outlined starting with an aryl cyano cycloalkanone and N-protected 3-aminoazetidine, which after reductive amination, Boc protection and hydrogenation produces the acylation precursor. Treatment with an activated Q species (e.g., activated (+)-DHP, activated (S)-oxa) and HCl-EtOAc provides the final product.

Some of the examples described within this invention were prepared as outlined in Scheme 2. Reductive amination of 4-cyano 4-phenylcyclohexanone and ammonium acetate provided both cis and trans isomers (~9:1) of 1-amino-4-cyano-4-phenylcyclohexanone, which after reductive amination with piperidonyl amides A and B furnished the targeted alpha 1a antagonists.

The 3-amino piperidinyl analogs were prepared from reductive amination of 3-aminopiperidine and 4-cyano-4-phenyl cyclohexanone, followed by Boc protection and hydrogenation of the CBZ protecting group. Acylation with an activated Q species provided the final products, Scheme 3.

Some of the required ketones were readily assembled following the sequence outlined in Scheme 4. For example, a substituted benzyl nitrile, sulphone, etc. could be added to methyl acrylate (or other substituted acrylates), submitted to Dieckman cyclization, hydrolyzed and decarboxylated providing appropriately substituted ketones. Further modifications of the ketones can be accomplished following the Dieckman cyclization, which provides the b-keto ester which can be either: (a) submitted to a reductive amination and carried on to final product, (b) enolized and alkylated then reductively aminated, deprotected and further manipulated providing further substituted analogs; or (c) hydrolyzed and decarboxylated and run through the above described conditions producing the desired antagonists.

Another strategy for the synthesis of some geminally disubstituted cyclic ketones, in particular, 4,4-disubstituted cyclohexanones was accomplished as outlined in Scheme 5 starting from benzophenone derivatives and substituted methyl vinyl ketones which under basic conditions lead to the 4,4-aryl cyclohex-2-en-1-ones in good yield. Subsequent hydrogenation, reductive amination and deprotection provided the appropriate acylation/alkylation precursors. Alternatively, the 4,4-aryl cyclohex-2-en-1-ones could be subjected to Michael addition of selected nucleophiles, alkylation or aldolyzation of the enolate of the resulting ketone then reductively aminated and carried through the standard chemical transformation to provide further elaborated antagonists.

The synthesis of some additional compounds of the present invention is described in Schemes 7 and 8. The 3-aminomethyl-3-hydroxyazetidine was assembled from the commercially available N-protected 3-hydroxyl azetidine as outlined Scheme 16. Swern oxidation of the alcohol with dimethylsulfoxide and oxalyl chloride provided the azetidinone. The zinc iodide catalyzed addition of TMSCN produced the cyanohydrin. Subsequent LAH reduction of the nitrile yielded the key intermediate required for the reductive aminations with the cyclohexanones. Deprotection of the N-dibenzylidine group and acylation with preferred activated "Q"-groups furnished the final targets.

The synthesis of the 4-amino-3-hydroxy-pyrrolidine intermediate began with 3,4-pyrroline. BOC protection of the amine followed by mCPBA oxidation provided the epoxidation. Subsequent sodium azide opening of the epoxide and triphenylphosphine/water mediated reduction produced 4-amino-N-1-(1,1-dimethylethoxycarbonyl)-3-hydroxypyrrolidine. This key amino intermediate was then alkylated by reductive amination reactions with cyclohexanones. Following the cleavage of the BOC protecting group acylation with preferred activated "Q"-groups furnished the final targets.

The activated termini species comprising the "Q" groups are readily prepared by one of ordinary skill in the art. For example, oxazolidinones are prepared and activated in general by published and well developed chemistry, in particular, of Evans. [Evans, D. A.; Nelson, J. V.; Taber, T. R. Top. Stereochem. 13, 1 (1982)] The starting materials, in general, are natural and unnatural amino acids. For instance, some of the preferred compounds are prepared from substituted phenyl glycine derivatives, which after reduction of the carboxylate and a phosgene equivalent mediated cyclization provides the substituted oxazolidinone ring system. Deprotonation with n-butyl lithium and addition to a THF solution of p-nitrophenylchloroformate produces the stable, isolable "activated" oxazolidinone (oxa).

Dihydropyrimidinones are prepared by condensation reaction of the aldehyde, urea and a 1,3-acetoacetate type derivative catalyzed by a Lewis Acid, a copper (I) species and acetic acid. Activation was accomplished by treatment with a strong base, for instance, LiN(TMS)$_2$, followed by addition to a THF solution of p-nitrophenylchloroformate.

Hydantoins and cycloimide were prepared in two chemical steps from ketones as outlined in the literature. More specifically, hydantoins were prepared according to known methodology, e.g., J. J. Edmunds et al., *J. Med. Chem.* 1995, 38, pp. 3759–3771; J. H. Poupart et al., *J. Chem. Res.* 1979, pp. 174–175. Saccharins were prepared according to known methods, e.g., page 40 and Examples 21 and 22 of PCT International Application Publication No. WO96/25934, published Aug. 29, 1996.

The dihydropyrimidinones and oxazolidinones were synthesized independently in racemic form, and then separated utilizing preparative chiral HPLC. Their optical rotations were recorded. Then they were activated and reacted with prerequisite amines. From the receptor binding studies, a preferred isomer was identified, the (+) rotational isomer in each case. The absolute configurations were determined to be (S) for both the dihydropyrimidinones and oxazolidinones by correlating their optical rotations with x-ray crystal structures obtained of fragments involved in the production of the antagonists.

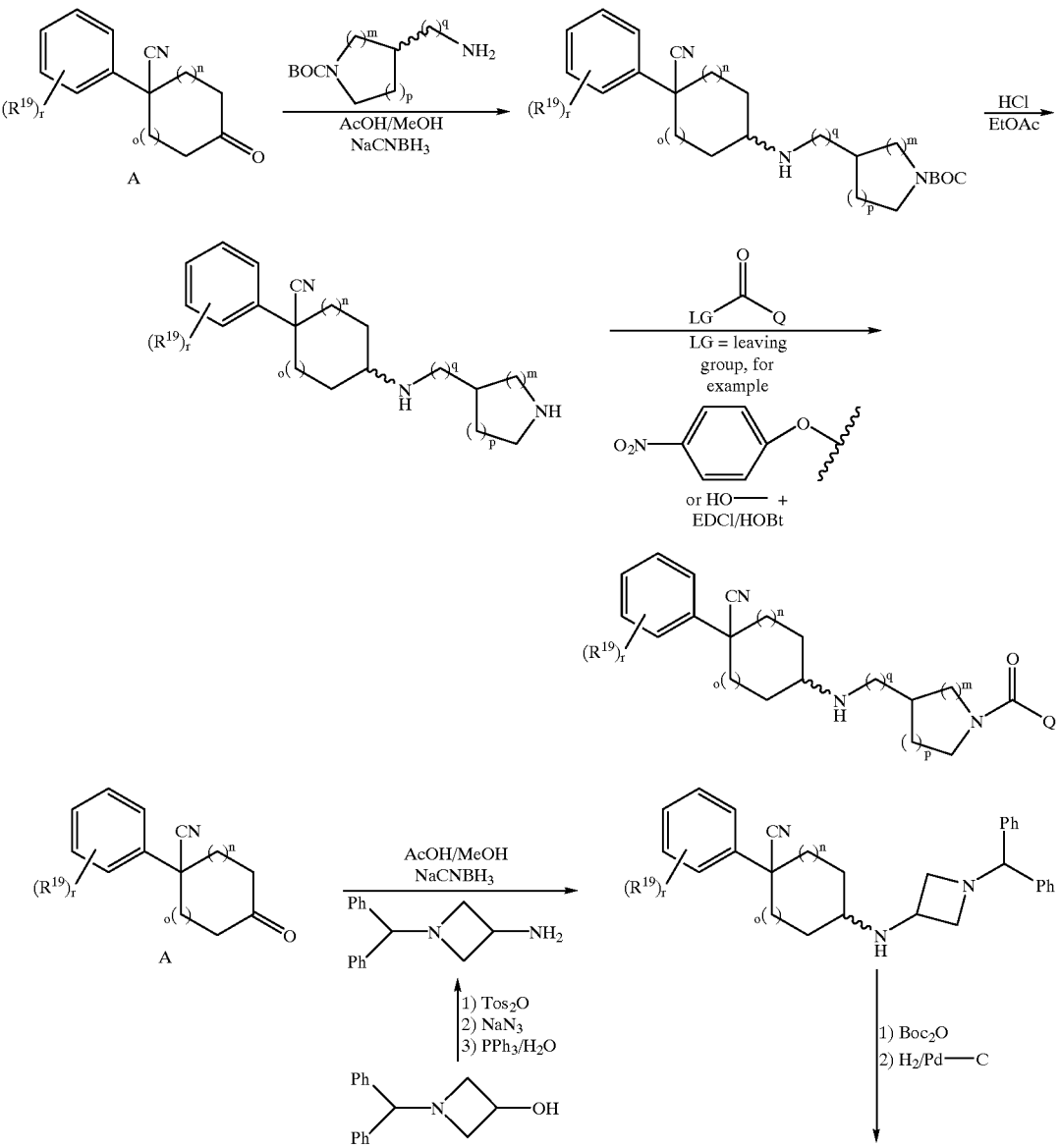

Scheme 1

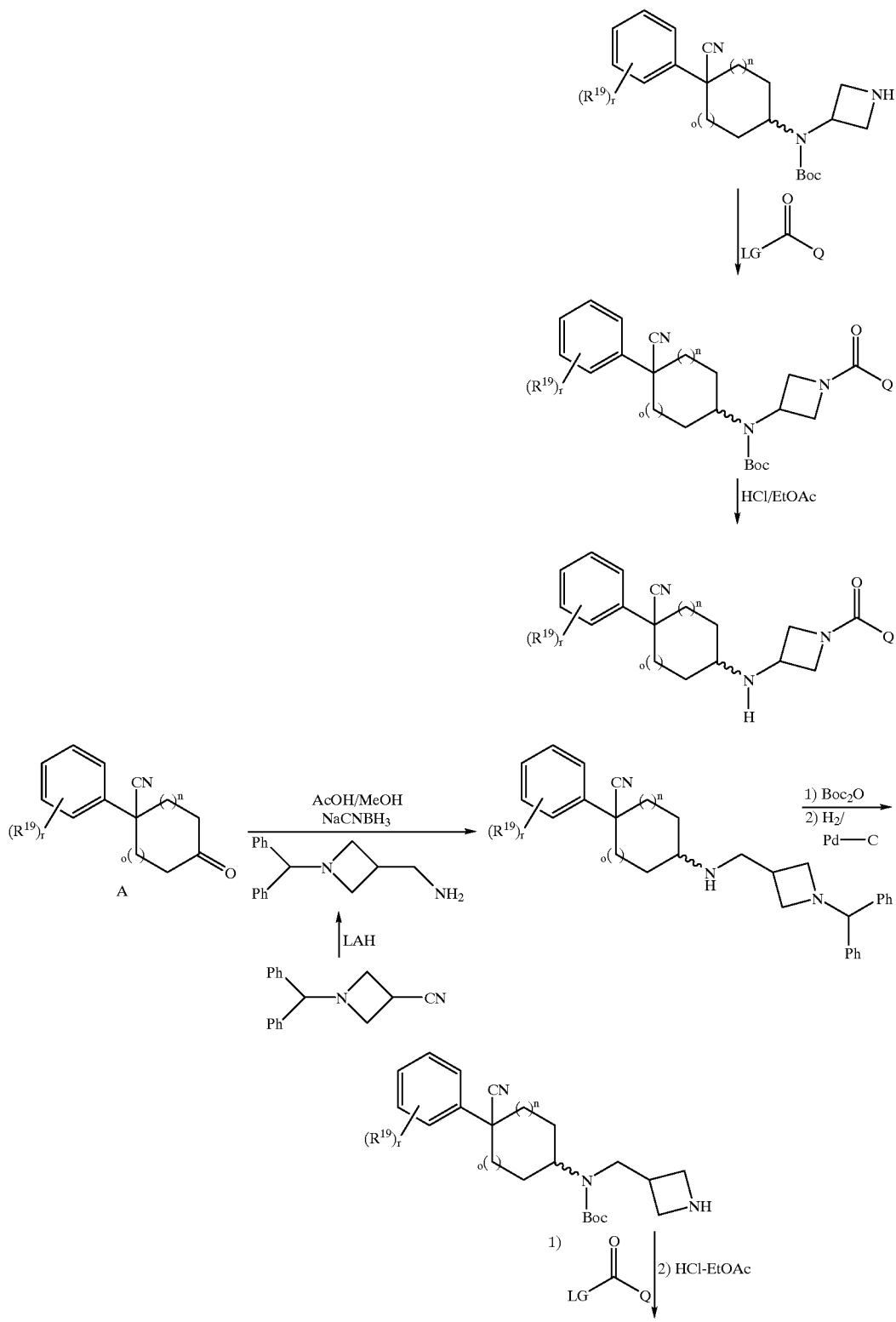

-continued
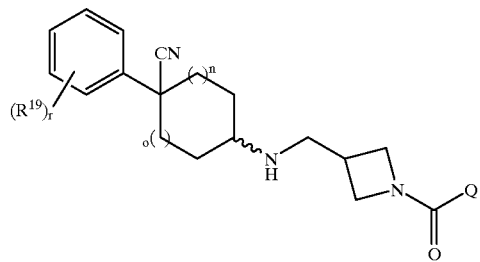
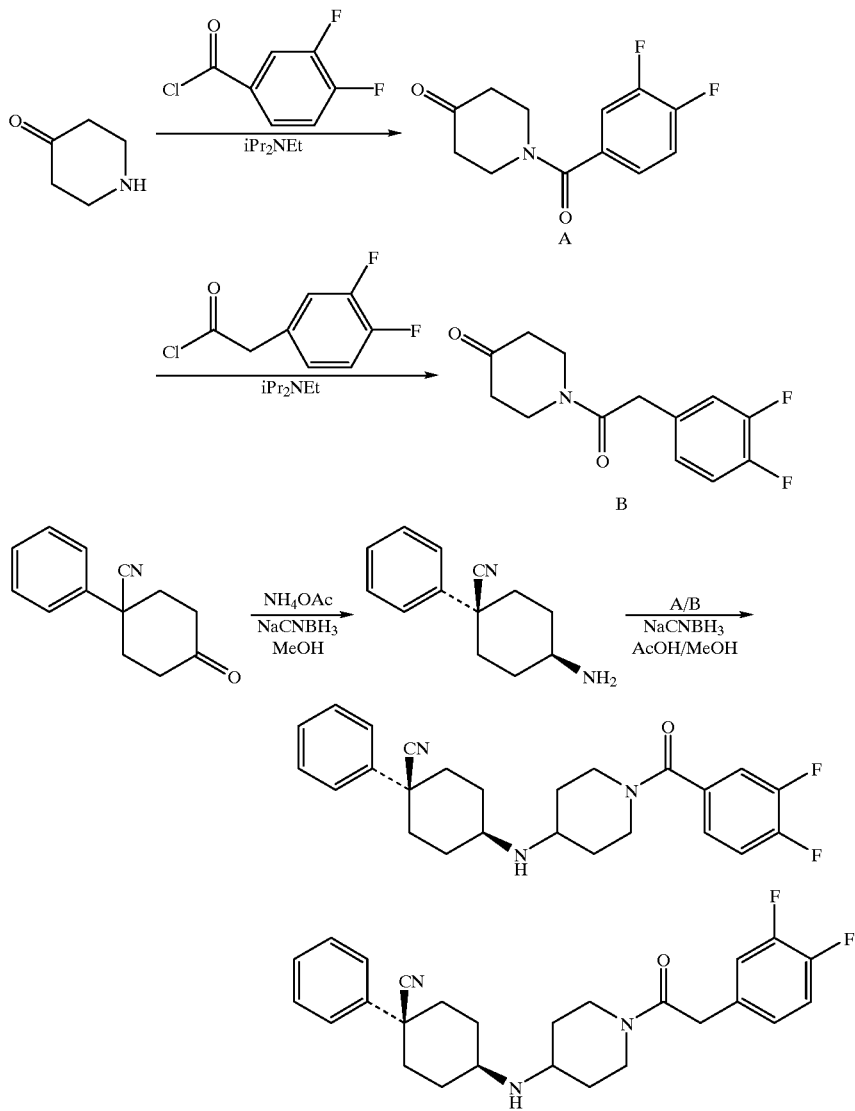

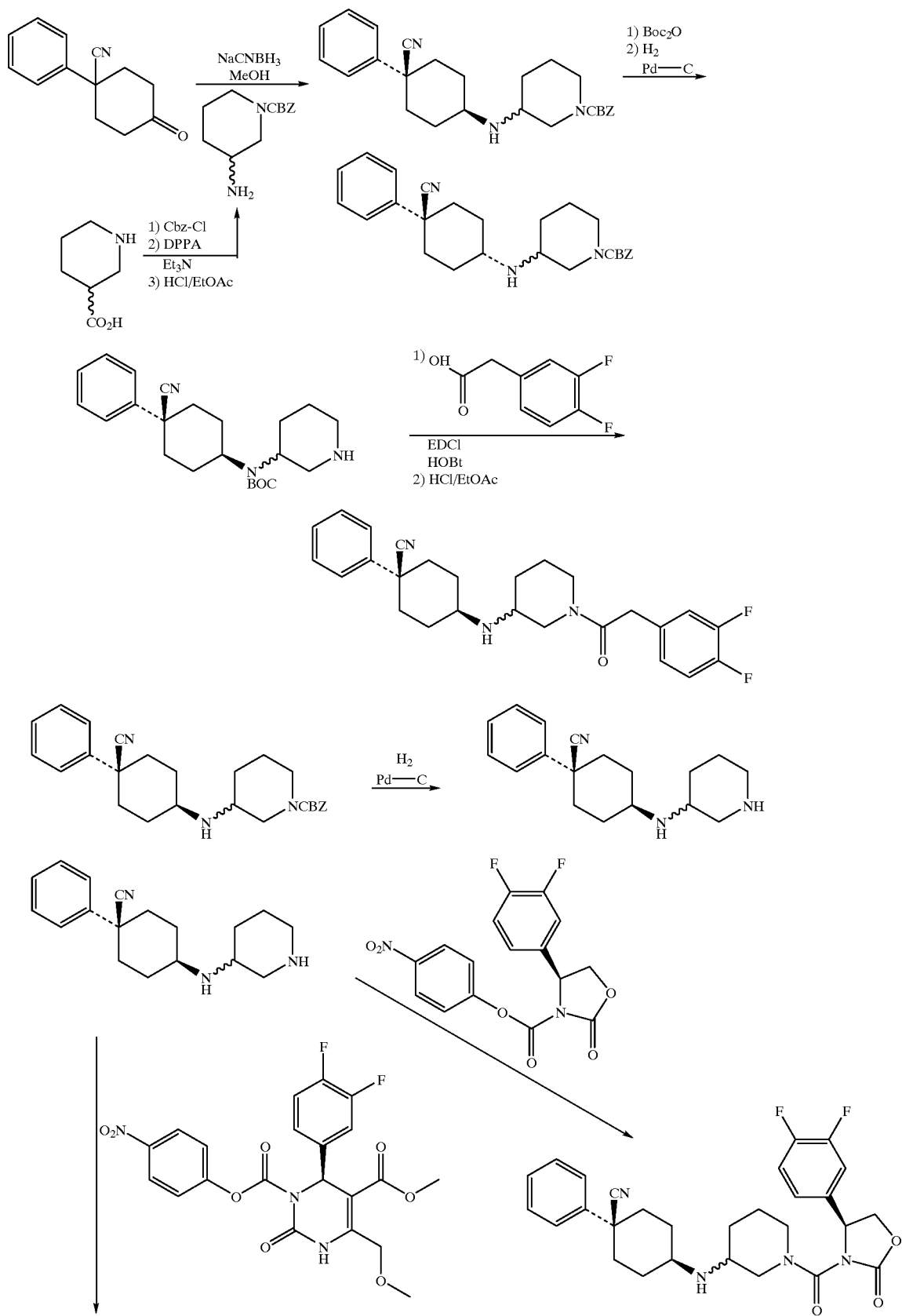

-continued
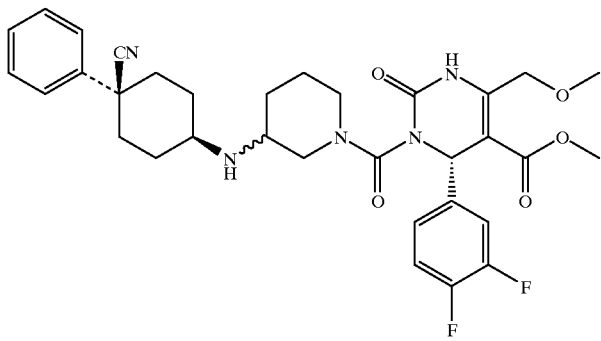
Scheme 4
For example,
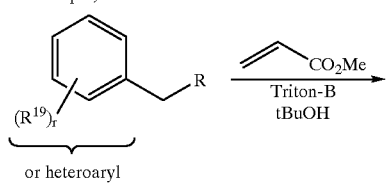
R = CN, SO$_2$alk, others
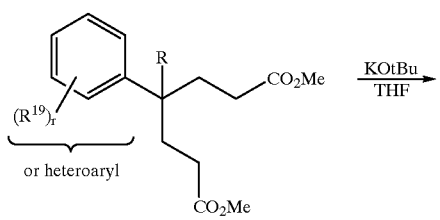
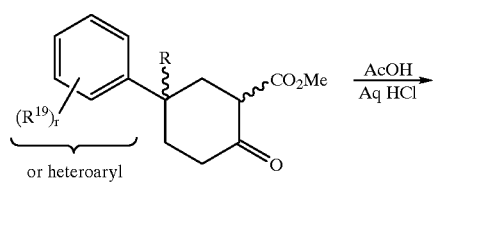
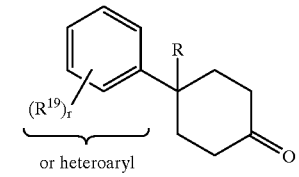
Scheme 5
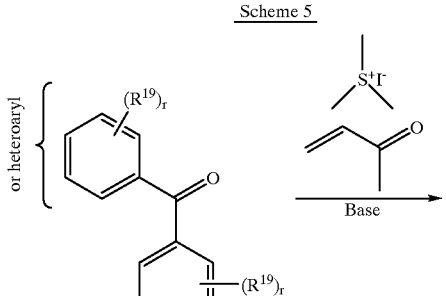
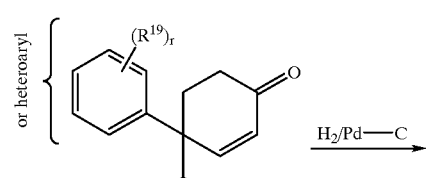
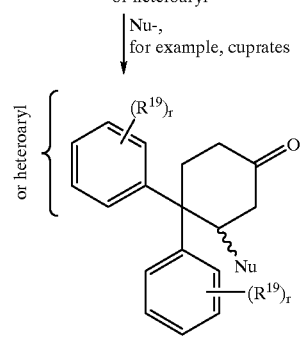

35
-continued
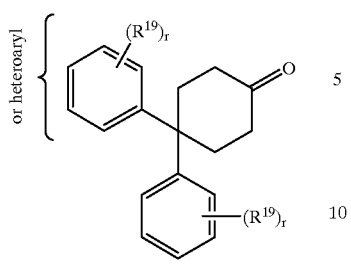
or heteroaryl
Scheme 6
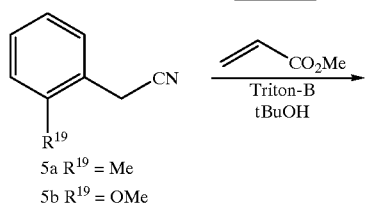
5a R¹⁹ = Me
5b R¹⁹ = OMe
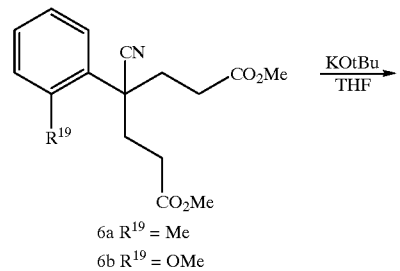
6a R¹⁹ = Me
6b R¹⁹ = OMe
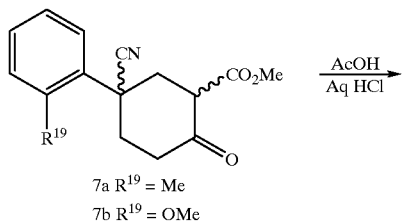
7a R¹⁹ = Me
7b R¹⁹ = OMe
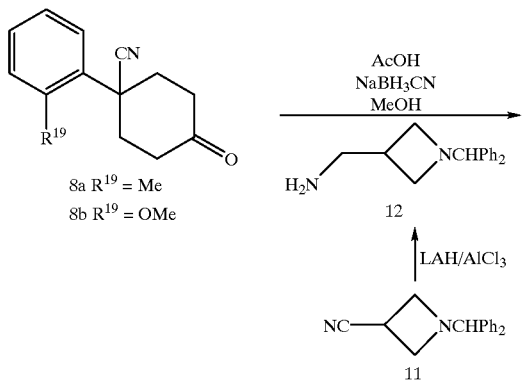
8a R¹⁹ = Me
8b R¹⁹ = OMe
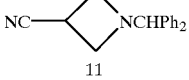
11
36
-continued
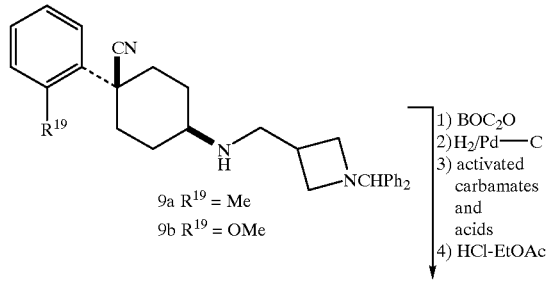
9a R¹⁹ = Me
9b R¹⁹ = OMe
1) BOC₂O
2) H₂/Pd—C
3) activated carbamates and acids
4) HCl-EtOAc
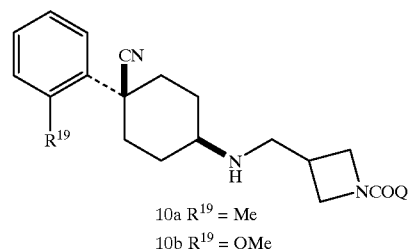
10a R¹⁹ = Me
10b R¹⁹ = OMe
Scheme 7
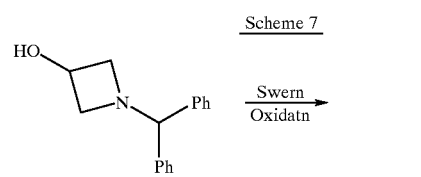
Swern Oxidatn
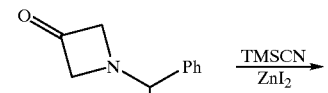
TMSCN / ZnI₂
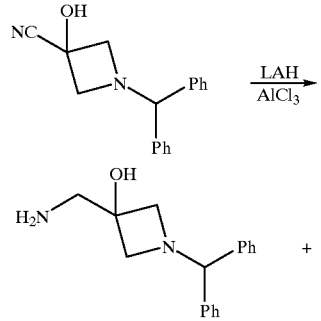
LAH / AlCl₃
   +
NaCNBH₃
AcOH, MeOH
1) H₂/Pd—C
2) Activated (+)-DHP or (S)-OXA

Scheme 8

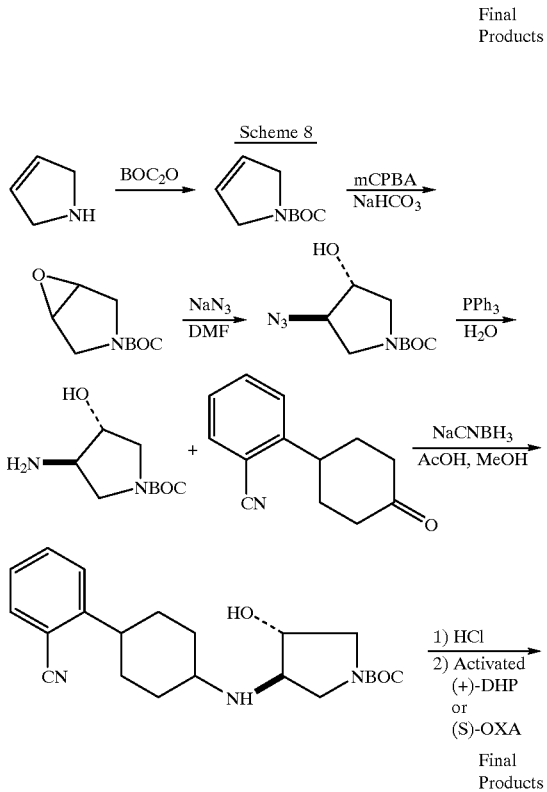

The following examples are provided to further define the invention without, however, limiting the invention to the particulars of these examples.

EXAMPLE 1

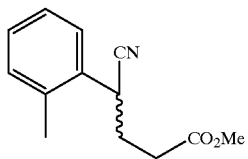

A

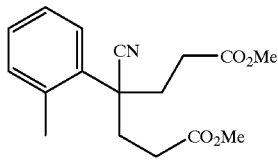

B

A: 5-nitrilo-4-o-tolyl-pentanoic acid methyl ester
B: 4-cyano-4-o-tolyl-heptanedioic acid dimethyl ester, (6a)

A solution of 2-methylbenzyl nitrile (25.0 g), methyl acrylate (75 mL) and Triton-B (40 mL) in t-butanol (90 mL) was refluxed (12 h). The solvent was removed in vacuo and submitted to SGC (SiO$_2$, 10 cm×30 cm, 0–15% EtOAc—hexane) affording the mono addition product and the desired bis addition compound (6a).

A: $^1$H NMR (CDCl$_3$, 300 MHz) 7.42 (m, 1 H, ArH), 7.20 (m, 3 H, ArH), 4.34 (dd, 1 H, CHCN), 3.69 (s, 3 H, OMe), 2.57 (m, 2 H), 2.37 (s, 3 H, Me), 2.16 (m, 2 H).

B: $^1$H NMR (CDCl$_3$, 300 MHz) 7.42 (m, 1 H, ArH), 7.20 (m, 3 H, ArH), 3.62 (s, 6 H, OMe), 2.57 (m, 4 H), 2.54 (s, 3 H, Me), 2.31 (m, 2 H).

EXAMPLE 2

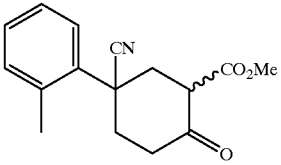

5-cyano-2-oxo-5-o-tolyl-cyclohexanecarboxylic acid methyl ester, (7a)

A solution of the diester (9.38 g, 29.4 mmol) in THF (200 mL) was treated with KOt-Bu (6.6 g, 58.74 mmol) at 0° C. then heated to reflux (20 min). The solvent was removed in vacuo and submitted to SGC (SiO$_2$, 6 cm×20 cm, 15% EtOAc—hexane) affording desired product and some decarboxylated material.

$^1$H NMR (CDCl$_3$, 300 MHz) consistent with assigned structure.

FABLRMS m/e 272.22 g/mole (M$^+$+H, C$_{16}$H$_{17}$NO$_3$=272 g/mole.)

EXAMPLE 3

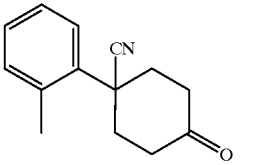

4-cyano(2-methylphenyl)-cyclohexan-1-one, (8a)

A solution of the ketoester (5.0 g, 18.4 mmol) in AcOH (100 mL) was treated with 10% aqueous H$_2$SO$_4$ (10 mL) at 0° C. then heated to reflux (24 h). The solvent was removed in vacuo, diluted with EtOAc (100 mL) and water (100 mL), partitioned, washed with brine (75 mL), dried (Na$_2$SO$_4$), filtered and concentrated in vacuo and submitted to SGC (SiO$_2$, 5 cm×20 cm, 0–15% EtOAc—hexane) affording the ketone.

$^1$H NMR (CDCl$_3$, 300 MHz) 7.24 (m, 4H, ArH), 2.95 (ddd, 1H, CHCN), 2.70 (s, 3 H, Me), 2.60 (m, 4 H), 2.20 (ddd, 2 H).

EXAMPLE 4

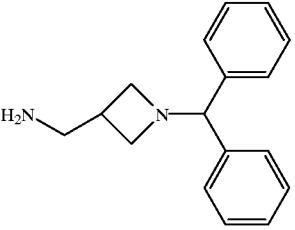

3-Aminomethyl N-diphenylmethyl azetidine, (12)

To a cooled solution of aluminum chloride (0.33 g, 2.41 mmol) in ether (50 mL) at −78° C. was added lithium aluminum hydride (2.41 ml, 2.41 mmol). After stirring 15 minutes at −78° C. the slurry was added a solution of 11(0.50 g, 2.01 mmol) in ether (10 mL) dropwise. The resulting mixture was stirred at room temperature for 2 hours. The solution was cooled to 0° C. and quenched with water (10 mL) dropwise followed by 25% NaOH solution (10 mL). The aqueous layer was extracted with EtOAc. The organics were dried over Na$_2$SO$_4$, filtered, and removed in vacuo. The crude product was not purified.

$^1$H NMR (CDCl$_3$, 300 MHz) 7.41–7.13 (m, 10 H), 4.32 (s, 1 H), 3.28 (t, 2 H), 2.88–2.79 (m, 4 H), 2.52–2.42(m, 1 H), 1.28 (s, 1 H).

EXAMPLE 5

Compound (9b)

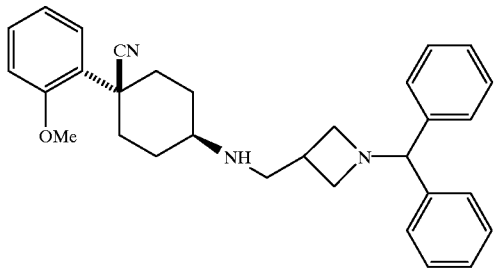

A solution of the ketone 8b (prepared in an analogous manner to 8a) (0.25 g, 1.09 mmol), amine 12 (0.275 g, 1.09 mmol) and acetic acid (0.327 g, 5.45 mmol) in MeOH (7 mL) was treated with NaBH$_3$CN (1.19 mL, 1.19 mmol, 1.0 M THF solution) at room temperature over a 1 hour period. The solvent was removed (12 h) in vacuo, diluted with DCM (25 mL) and saturated aqueous sodium bicarbonate (25 mL), partitioned, extracted with DCM (2×25 mL), washed with saturated aqueous sodium bicarbonate (2×25 mL) and brine (50 mL), dried (Na$_2$SO$_4$), filtered and concentrated in vacuo and submitted to PCTLC (SiO$_2$, 4 mm, 90/10/1 CHCl$_3$-MeOH-NH$_4$OH) the titled amine.

$^1$H NMR (CDCl$_3$, 400 MHz) 7.41–7.38 (m, 4 H), 7.33–7.28 (m, 4 H), 7.22 (s, 2 H), 7.19–7.14 (m, 2 H), 6.98–6.90 (m, 2 H), 4.33 (s, 1 H), 3.91 (3 H), 3.36–3.31 (t, 2 H), 2.88–2.74 (m, 5 H), 2.60–2.55 (m, 2 H), 1.89–1.80 (m, 2 H), 1.72–1.64 (m, 2 H).

Anal. Calcd for C$_{31}$H$_{35}$N$_3$O$_1$·0.15 CHCl$_3$: C=77.37, H=7.33, N=8.69. Found: C=77.54, H=7.43, N=9.08.

MS (FAB) 466 (M+1)

EXAMPLE 6

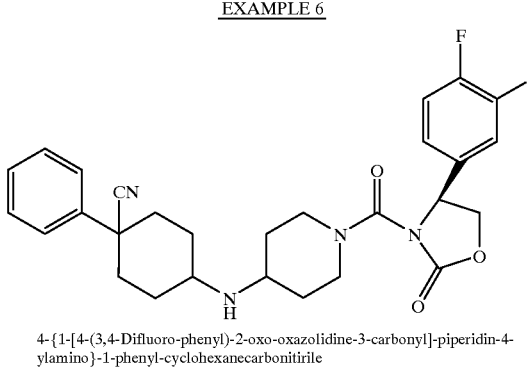

4-{1-[4-(3,4-Difluoro-phenyl)-2-oxo-oxazolidine-3-carbonyl]-piperidin-4-ylamino}-1-phenyl-cyclohexanecarbonitirile a. 4-(1-Benzyl-piperidin-4-ylamino)-1-Phenyl-cyclohexanecarbo-nitrile A mixture of 4-cyano-4-phenyl-cyclohexanone (1.5 g, 7.5 mmol) and 4-amino-N-benzylpiperidine (1.5 g, 7.9 mmol) in 50 ml of benzene was stirred at reflux for 2 h in presence of catalytic amount of p-toluenesulfonic acid. The reaction mixture was concentrated in vacuo to provide a white solid, which was redissolved in 50 ml of EtOH and stirred with NaBH$_4$ (0.60 g, 160 mmol) for 12 h at 25° C. Reaction mixture was diluted with 200 ml of EtOAc and washed with brine several times. Organic layer was dried over MgSO$_4$ and concentrated in vacuo, to provide oily residue, which was identified as the desired product by NMR analysis and subjected to the following reaction without any further purification.

b. (4-cyano-4-phenyl-cyclohexyl)-piperidin-4-yl-carbamic acidtert-butyl ester

A solution of the amine and di-tert-butyl dicarbonate (1.6 g, 7.3 mmol) was dissolved in 30 ml of DMF and stirred at 80° C. for 12 h. The reaction mixture was diluted in EtOAc and washed with brine several times. Organic layer was separated and concentrated in vacuo, to provide oily residue, which was subjected to column chromatography (50% Hexane/EtOAc) to yield (4-cyano-4-phenyl-cyclohexyl)-1-benzyl-piperidin-4-yl-carbamic acid tert-butyl ester as an oil. The amine obtained was dissolved in 100 ml of MeOH and stirred with catalytic amount of 10% Pd/C under atmosphere pressure of H$_2$. The reaction mixture was filtered and concentrated in vacuo to provide the desired product as an oil.

c. 4-{1-[4-(3,4-Difluoro-phenyl)-2-oxo-oxazolidine-3-carbonyl]-piperidin-4-ylamino}-1-phenyl-cyclohexanecarbonitrile To a solution of 4-(3,4-difluoro-phenyl)-2-oxo-oxazolidine-3-carboxylic acid 4-nitrophenyl ester (80 mg, 0.21 mmol) in 5 ml of THF was added (4-cyano-4-phenyl-cyclohexyl)-piperidin-4-yl-carbamic acid tert-butyl ester (150 mg, 0.40 mmol) in a portion and the resulting solution was stirred for 12 h at 25° C. Reaction mixture was concentrated in vacuo, yielding a yellow oil, which was subjected to column chromatography (50% Hexane/EtOAc) to provide the tert-butyl ester of the desired product as a colorless oil. The product obtained was dissolved in 5 ml of EtOAc and 1 ml of 1N HCl-Et$_2$O to afford a white solid of the product as the HCl salt: mp 181–192 C; Anal. Calc. For C$_{27}$H$_{28}$F$_2$N$_4$O$_3$·1.0HCl requires C, 61.70; H, 5.73; N, 10.28. Found: C, 59.48; H, 5.41; N, 10.34.

Following the schemes and examples described herein, the compounds shown in Table 1 were prepared.

TABLE 1

| Compound | cis/trans | A |
|---|---|---|
| 1 | cis | H |
| 2 | cis | (3,4-difluorophenacyl) |
| 3 | cis | CBZ |
| 4 | trans | CBZ |

Compound 1:

| | |
|---|---|
| FABLRMS: | 284.09 g/mole |
| HPLC R.T.: | 5.73 min. |
| Elemental Analysis: | Calc. for 2.0 HCl |
| | Solvate mol. wt. = 613.14 g/mole |

TABLE 1-continued

|  |  |
|---|---|
|  | Calc: C = 60.67% H = 7.82% N = 11.79% |
|  | Obs: C = 60.34% H = 7.58% N = 11.56% |
| Compound 2: |  |
| FABLRMS: | 438.03 g/mole |
| HPLC R.T.: | 9.25 min. |
| Elemental Analysis: | Calc. for 1.0 HCl; 0.45 H$_2$O; 0.15 EtOAc |
|  | Solvate mol. wt. = 495.32 g/mole |
|  | Calc: C = 64.50% H = 6.53% N = 8.48% |
|  | Obs: C = 64.47% H = 6.47% N = 8.46% |
| Compound 3: |  |
| FABLRMS: | 418.22 g/mole |
| HPLC R.T.: | 8.71 min. |
| Elemental Analysis: | Calc. for 1.0 HCl; 0.95 H$_2$O; 0.45 EtOAc |
|  | Solvate mol. wt. = 528.34/mole |
|  | Calc: C = 63.20% H = 6.91% N = 7.95% |
|  | Obs: C = 63.10% H = 6.60% N = 8.01% |
| Compound 4: |  |
| FABLRMS: | 418.17 g/mole |
| HPLC R.T.: | 8.50 min. |
| Elemental Analysis: | Calc. for 1.0 HCl |
|  | Solvate mol. wt. = 454.02 g/mole |
|  | Calc: C = 68.78% H = 7.10% N = 9.26% |
|  | Obs: C = 68.84% H = 7.26% N = 8.86% |

EXAMPLE 7

Mixture of (4S)-4-(3,4-difluorophenyl)-6-methoxymethyl-2-oxo-1,2,3,4-tetrahydropyrimidine and 4S-4-(3,4-difluorophenyl)-6-methoxymethyl-2-oxo-2,3,4,5-tetrahydropyrimidine

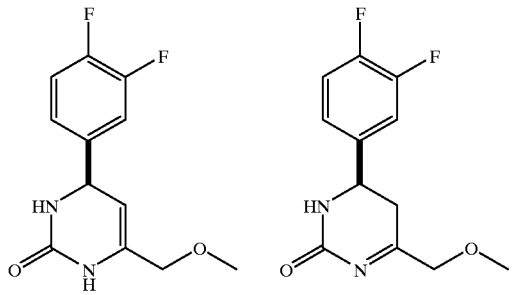

To a solution of (+)-4-(3,4-difluorophenyl)-6-methoxymethyl-2-oxo-1,2,3,4-tetrahydropyrimidine-5-carboxylic acid methyl ester (4.63 g, 14.7 mmol) in a methanol (100 ml) was added sodium hydroxide (2.94 g, 73.6 mmol). The resulting mixture was refluxed at 90° C. for 16 hours. After cooling to room temperature the solvent was removed in vacuo. The solid was dissolved in CH$_2$Cl$_2$ and H$_2$O then neutralized with 10% aqueous HCl solution. The organic layer was dried over Na$_2$SO$_4$, concentrated, and purified by PCTLC (7% MeOH in CHCl$_3$ with 2% NH$_4$OH) to afford a 2.65 g mixture of the title compounds (71% yield). The $^1$H NMR was consistent with the assigned structure.

MS (FAB) 255 (M+1)

EXAMPLE 8

Mixture of (4S)-4-(3,4-difluorophenyl)-6-methoxymethyl-2-oxo-1,2,3,4-tetrahydropyrimidine and 4S-4-(3,4-difluorophenyl)-6-methoxymethyl-2-oxo-2,3,4,5-tetrahydropyrimidine

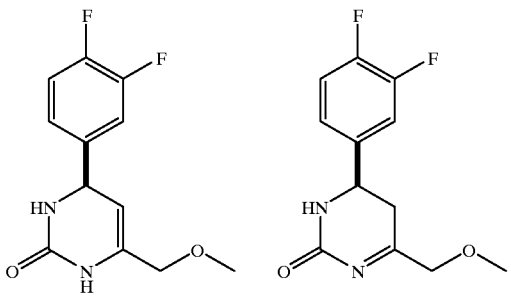

To a solution of (+)-4-(3,4-difluorophenyl)-6-methoxymethyl-2-oxo-1,2,3,4-tetrahydropyrimidine-5-carboxylic acid methyl ester (5.36 g, 17.0 mmol) in a methanol (150 ml) was added 1N NaOH (10 ml). The resulting mixture was refluxed at 90° C. for 16 hours. After cooling to room temperature the solvent was removed in vacuo. The solid was dissolved in CH$_2$Cl$_2$ and H$_2$O then neutralized with 10% aqueous HCl solution. The organic layer was dried over Na$_2$SO$_4$, concentrated, and purified by PCTLC (7% MeOH in CHCl$_3$ with 2% NH$_4$OH) to afford a 2.35 g mixture of the title compounds (54% yield). The $^1$H NMR was consistent with the assigned structure.

MS (FAB) 255 (M+1)

EXAMPLE 9

(4S)-4-(3,4-Difluorophenyl)-6-methoxymethyl-3-(4-nitrophenoxycarbonyl)-2-oxo-1,2,3,4-tetrahydropyrimidine-5-carboxylic acid methyl ester

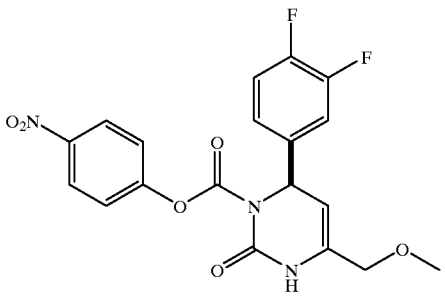

The title compound was prepared by treating the mixture obtained from Example 7 or Example 8 (1.93 g, 7.59 mmol) with lithium diisopropylamide (2.0M THF solution, 1.1 equivalents) in THF at −78° C. for 20 minutes followed by the rapid addition of 4-nitrophenyl chloroformate (1.5 equivalents) in THF. 0.488 g of the title compound was obtained in a 15% yield. The $^1$H NMR was consistent with the assigned structure.

EXAMPLE 10

Mixture of (4R)-4-(3,4-difluorophenyl)-6-methoxymethyl-2-oxo-1,2,3,4-tetrahydropyrimidine and 4R-4-(3,4-difluorophenyl)-6-methoxymethyl-2-oxo-2,3,4,5-tetrahydropyrimidine

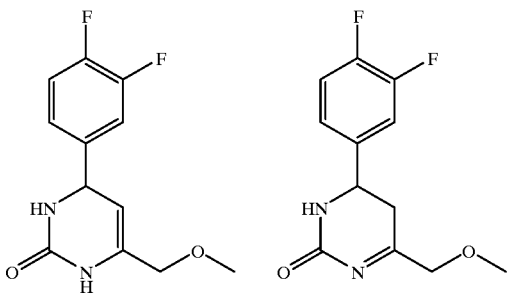

The title compounds were prepared from 4R-4-(3,4-difluorophenyl)-6-methoxymethyl-2-oxo-1,2,3,4-tetrahydropyrimidine-5-carboxylic acid methyl ester (5.0 g, 17.7 mmol) using the procedure described in Example 7. A mixture of 2.0 g of the title compounds was obtained in 50% yield. The $^1$H NMR was consistent with the assigned structure.

MS (FAB) 255 (M+1)

Compounds of the invention can be prepared by reacting the products obtained in Example 9 in accordance with procedures and schemes described above. The compound of Example 9 can, for example, be reacted with an aminocyclohexylpiperidine or aminocyclohexylpyrrolidine in accordance with Schemes 1 and 3 to obtain the desired compounds. Compounds of the invention can also be prepared by preparing a nitrophenoxy derivative of the compound of Example 10 in accordance with the procedure set forth in Example 9 and then reacting the derivative with an aminocyclohexylpiperidine or aminocyclohexylpyrrolidine as set forth in Schemes 1 and 3 to obtain compounds of the invention.

EXAMPLE 11

As a specific embodiment of an oral composition, 100 mg of the compound of Example 6 is formulated with sufficient finely divided lactose to provide a total amount of 580 to 590 mg to fill a size O hard gel capsule.

EXAMPLE 12

Screening Assay: Alpha 1a Adrenergic Receptor Binding

Membranes prepared from the stably transfected human alpha 1a cell line (ATCC CRL 11140) were used to identify compounds that bind to the human alpha 1a adrenergic receptor. These competition binding reactions (total volume=200 µl) contained 50 mM Tris-HCl pH. 7.4, 5 mM EDTA, 150 mM NaCl, 100 pM [$^{125}$I]-HEAT, membranes prepared from the alpha 1a cell line and increasing amounts of unlabeled ligand. Reactions were incubated at room temperature for one hour with shaking. Reactions were filtered onto Whatman GF/C glass fiber filters with a Inotec 96 well cell harvester. Filters were washed three times with ice cold buffer and bound radioactivity was determined (Ki). Representative compounds of the present invention were found to have Ki values≦50 nM.

EXAMPLE 13

Selective Binding Assays

Membranes prepared from stably transfected human alpha 1d and alpha 1b cell lines (ATCC CRL 11138 and CRL 11139, respectively) were used to identify compounds that selectively bind to the human alpha 1a adrenergic receptor. These competition binding reactions (total volume=200 µl) contained 50 mM Tris-HCl pH. 7.4, 5 mM EDTA, 150 mM NaCl, 100 pM [$^{125}$I]-HEAT, membranes prepared from cell lines transfected with the respective alpha 1 subtype expression plasmid and increasing amounts of unlabeled ligand. Reactions were incubated at room temperature for one hour with shaking. Reactions were filtered onto Whatman GF/C glass fiber filters with a Inotec 96 well cell harvester. Filters were washed three times with ice cold buffer and bound radioactivity was determined (Ki).

EXAMPLE 14

EXEMPLARY COUNTERSCREENS

1. Assay Title: Dopamine D2, D3, D4 in vitro screen

Objective of the Assay:

The objective of this assay is to eliminate agents which specifically affect binding of [3H] spiperone to cells expressing human dopamine receptors D2, D3 or D4.

Method:

Modified from VanTol et al (1991); Nature (Vol 350) Pg 610–613.

Frozen pellets containing specific dopamine receptor subtypes stably expressed in clonal cell lines are lysed in 2 ml lysing buffer (10 mM Tris-HCl/5 mM Mg, pH 7.4). Pellets obtained after centrifuging these membranes (15' at 24,450 rpm) are resuspended in OmM Tris-HCl pH 7.4 containing EDTA, MgCl[21], KCl, NaCl, CaCl[2] and ascorbate to give a 1 Mg/mL suspension. The assay is initiated by adding 50–75 µg membranes in a total volume of 500 µl containing 0.2 nM [3H]-spiperone. Non-specific binding is defined using 10 µM apomorphine. The assay is terminated after a 2 hour incubation at room temperature by rapid filtration over GF/B filters presoaked in 0.3% PEI, using 50 mM Tris-HCl pH 7.4.

2. Assay Title: Serotonin 5HT1a

Objective of the Assay

The objective of this assay is to eliminate agents which specifically affect binding to cloned human 5HT1a receptor Method:

Modified from Schelegel and Peroutka *Biochemical Pharmacology* 35: 1943–1949 (1986).

Mammalian cells expressing cloned human 5HT1a receptors are lysed in ice-cold 5 mM Tris-HCl, 2 mM EDTA (pH 7.4) and homogenized with a polytron homogenizer. The homogenate is centrifuged at 1000×g for 30', and then the supernatant is centrifuged again at 38,00×g for 30'. The binding assay contains 0.25 nM [3H]8-OH-DPAT (8-hydroxy-2-dipropylamino-1,2,3,4-tetrahydronaphthalene) in 50 mM Tris-HCl, 4 mM CaCl2 and 1 mg/ml ascorbate. Non-specific binding is defined using 10 µM propranolol. The assay is terminated after a 1 hour incubation at room temperature by rapid filtration over GF/Cfilters

EXAMPLE 15

EXEMPLARY FUNCTIONAL ASSAYS

In order to confirm the specificity of compounds for the human alpha 1a adrenergic receptor and to define the biological activity of the compounds, the following functional tests may be performed:

1. In vitro Rat, Dog and Human Prostate and Dog Urethra Taconic Farms Sprague-Dawley male rats, weighing 250–400 grams are sacrificed by cervical dislocation under anesthesia (methohexital; 50 mg/kg, i.p.). An incision is made into the lower abdomen to remove the ventral lobes of the prostate. Each prostate removed from a mongrel dog is cut into 6–8 pieces longitudinally along the urethra opening and stored in ice-cold oxygenated Krebs solution overnight before use if necessary. Dog urethra proximal to prostate is cut into approximately 5 mm rings, the rings are then cut open for contractile measurement of circular muscles. Human prostate chips from transurethral surgery of benign prostate hyperplasia are also stored overnight in ice-cold Krebs solution if needed.

The tissue is placed in a Petri dish containing oxygenated Krebs solution [NaCl, 118 mM; KCl, 4.7 mM; $CaCl_2$, 2.5 mM; $KH_2PO_{4,\ 1.2}$ mM; $MgSO_{4,\ 1.2}$ mM; $NaHCO_3$, 2.0 mM; dextrose, 11 mM] warmed to 37° C. Excess lipid material and connective tissue are carefully removed. Tissue segments are attached to glass tissue holders with 4-0 surgical silk and placed in a 5 ml jacketed tissue bath containing Krebs buffer at 37° C., bubbled with 5% $CO_2$/95% $O_2$. The tissues are connected to a Statham-Gould force transducer; 1 gram (rat, human) or 1.5 gram (dog) of tension is applied and the tissues are allowed to equilibrate for one hour. Contractions are recorded on a Hewlett-Packard 7700 series strip chart recorder.

After a single priming dose of 3 $\mu$M (for rat), 10 $\mu$M (for dog) and 20 $\mu$M (for human) of phenylephrine, a cumulative concentration response curve to an agonist is generated; the tissues are washed every minutes for one hour. Vehicle or antagonist is added to the bath and allowed to incubate for one hour, then another cumulative concentration response curve to the agonist is generated.

$EC_{50}$ values are calculated for each group using GraphPad Inplot software. pA2 (–log Kb) values were obtained from Schild plot when three or more concentrations were tested. When less than three concentrations of antagonist are tested, $K_b$ values are calculated according to the following formula $$K_b = \frac{[B]}{x-1},$$

where x is the ratio of $EC_{50}$ of agonist in the presence and absence of antagonist and [B] is the antagonist concentration.

2. Measurement of Intra-Urethral Pressure in Anesthetized Dogs

PURPOSE: Benign prostatic hyperplasia causes a decreased urine flow rate that may be produced by both passive physical obstruction of the prostatic urethra from increased prostate mass as well as active obstruction due to prostatic contraction. Alpha adrenergic receptor antagonists such as prazosin and terazosin prevent active prostatic contraction, thus improve urine flow rate and provide symptomatic relief in man. However, these are non-selective alpha 1 receptor antagonists which also have pronounced vascular effects. Because we have identified the alpha 1a receptor subtype as the predominent subtype in the human prostate, it is now possible to specifically target this receptor to inhibit prostatic contraction without concomitant changes in the vasculature. The following model is used to measure adrenergically mediated changes in intra-urethral pressure and arterial pressure in anesthetized dogs in order to evaluate the efficacy and potency of selective alpha adrenergic receptor antagonists. The goals are to: 1) identify the alpha 1 receptor subtypes responsible for prostatic/urethral contraction and vascular responses, and 2) use this model to evaluate novel selective alpha adrenergic antagonists. Novel and standard alpha adrenergic antagonists may be evaluated in this manner.

METHODS: Male mongrel dogs (7–12 kg) are used in this study. The dogs are anesthetized with pentobarbital sodium (35 mg/kg, i.v. plus 4 mg/kg/hr iv infusion). An endotracheal tube is inserted and the animal ventilated with room air using a Harvard instruments positive displacement large animal ventilator. Catheters (PE 240 or 260) are placed in the aorta via the femoral artery and vena cava via the femoral veins (2 catheters, one in each vein) for the measurement of arterial pressure and the administration of drugs, respectively. A supra-pubic incision ~½ inch lateral to the penis is made to expose the urethers, bladder and urethra. The urethers are ligated and cannulated so that urine flows freely into beakers. The dome of the bladder is retracted to facilitate dissection of the proximal and distal urethra. Umbilical tape is passed beneath the urethra at the bladder neck and another piece of umbilical tape is placed under the distal urethra approximately 1–2 cm distal to the prostate. The bladder is incised and a Millar micro-tip pressure transducer is advanced into the urethra. The bladder incision is sutured with 2-0 or 3-0 silk (purse-string suture) to hold the transducer. The tip of the transducer is placed in the prostatic urethra and the position of the Millar catheter is verified by gently squeezing the prostate and noting the large change in urethral pressure.

Phenylephrine, an alpha 1 adrenergic agonist, is administered (0.1–100 ug/kg, iv; 0.05 ml/kg volume) in order to construct dose response curves for changes in intra-urethral and arterial pressure. Following administration of increasing doses of an alpha adrenergic antagonist (or vehicle), the effects of phenylephrine on arterial pressure and intra-urethral pressure are re-evaluated. Four or five phenylephrine dose-response curves are generated in each animal (one control, three or four doses of antagonist or vehicle). The relative antagonist potency on phenylephrine induced changes in arterial and intra-urethral pressure are determined by Schild analysis. The family of averaged curves are fit simultaneously (using ALLFIT software package) with a four parameter logistic equation constraining the slope, minimum response, and maximum response to be constant among curves. The dose ratios for the antagonist doses (rightward shift in the dose-response curves from control) are calculated as the ratio of the $ED_{50}$'s for the respective curves. These dose-ratios are then used to construct a Schild plot and the Kb (expressed as ug/kg, iv) determined. The Kb (dose of antagonist causing a 2-fold rightward shift of the phenylephrine dose-response curve) is used to compare the relative potency of the antagonists on inhibiting phenylephrine responses for intra-urethral and arterial pressure. The relative selectivity is calculated as the ratio of arterial pressure and intra-urethral pressure Kb's. Effects of the alpha 1 antagonists on baseline arterial pressure are also monitored. Comparison of the relative antagonist potency on changes in arterial pressure and intra-urethral pressure provide insight as to whether the alpha receptor subtype responsible for increasing intra-urethral pressure is also present in the systemic vasculature. According to this method, one is able to confirm the selectivity of alpha 1a adrenergic receptor antagonists that prevent the increase in intra-urethral pressure to phenylephrine without any activity at the vasculature.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of the formula:

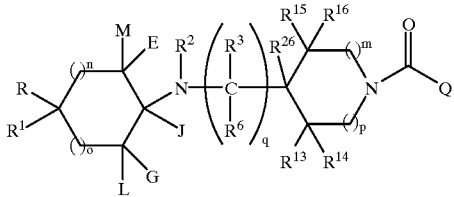

wherein Q is

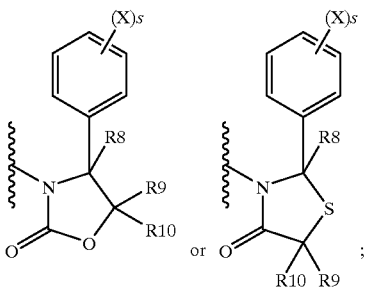

$R^1$ is selected from unsubstituted, mono- or poly-substituted phenyl wherein the substituents on the phenyl are independently selected from halogen, $CF_3$, cyano, nitro, $N(R^{17})_2$, $NR^{17}COR^{18}$, $NR^{17}CON(R^{18})_2$, $NR^{17}SO_2R^7$, $NR^{17}SO_2N(R^{18})2$, $OR^7$, $(CH_2)_{0-4}CO_2R^{17}$, $(CH_2)_{0-4}CON(R^{17})_2$, $(CH_2)_{0-4}SO_2N(R^{17})_2$, $(CH_2)_{0-4}SO_2R^7$ or $C_{1-4}$ alkyl; or unsubstituted, mono- or poly-substituted pyridyl, pyrazinyl, thienyl, thiazolyl, furanyl, quinazolinyl or naphthyl wherein the substituents on the pyridyl, pyrazinyl, thienyl, thiazolyl, furanyl, quinazolinyl or naphthyl are independently selected from $CF_3$, cyano, nitro, $N(R^{17})_2$, $(CH_2)_{0-4}CO_2R^{17}$, $(CH_2)_{0-4}CON(R^{17})_2$, $(CH_2)_{0-4}SO_2N(R^7)_2$, phenyl, $OR^7$, halogen, $C_{1-4}$ alkyl or $C_{3-8}$ cycloalkyl;

R is selected from hydrogen, cyano, $OR^7$, $CO_2R^{17}$, $CON(R^{17})_2$, $SO_2R^7$, $SO_2N(R^{17})_2$, tetrazole, isooxadiazole, unsubstituted, mono- or poly-substituted phenyl wherein the substituents on the phenyl are independently selected from halogen, cyano, nitro, $OR^7$, $(CH_2)_{0-4}CO_2R^{17}$, $(CH_2)_{0-4}CON(R^{17})_2$, $(R^{17})_2$, $NR^{17}COR^7$, $NR^{17}CON(R^{18})_2$, $NR^{17}SO_2R^7$, $NR^{17}SO_2N(R^{18})_2$, $(CH_2)_{0-4}SO_2N(R_{17})_2$, $(CH_2)_{0-4}SO_2R^7$ or $C_{1-4}$ alkyl; or unsubstituted, mono- or poly-substituted pyridyl, thienyl, furanyl or naphthyl wherein the substituents on the pyridyl, thienyl, furanyl or naphthyl are independently selected from $CF_3$, $(CH_2)_{0-4}CO_2R^{17}$, $(CH_2)_{0-4}CON(R^{17})_2$, $(CH_2)_{0-4}SO_2N(R^{17})_2$,$(CH_2)_{0-4}SO_2R^7$, phenyl, $OR^7$, halogen, $C_{1-4}$ alkyl or $C_{3-8}$ cycloalkyl;

E, G, L and M are each independently selected from hydrogen, $C_{1-8}$ alkyl, $C_{3-8}$ cycloalkyl, $(CH_2)_{0-4}OR^7$, $(CH_2)_{0-4}N(R^{17})_2$, $(CH_2)_{0-4}CN$, $(CH_2)_{0-4}CF_3$, $(CH_2)_{0-4}CO_2R^7$, $(CH_2)_{0-4}CON(R^{17})_2$, $(CH_2)_{0-4}SO_2R^{17}$ or $(CH_2)_{0-4}SO_2N(R^{17})_2$;

J is selected from hydrogen, $C_{1-8}$ alkyl, $C_{3-8}$ cycloalkyl, $(CH_2)_{1-4}OR^7$, $(CH_2)_{1-4}N(R^{17})_2$, $(CH_2)_{1-4}CN$, $(CH_2)_{0-4}CF_3$, $(CH_2)_{0-4}CO_2R^7$, $(CH_2)_{0-4}CON(R^{17})_2$, $(CH_2)_{0-4}SO_2R^{17}$ or $(CH_2)_{0-4}SO_2N(R^{17})_2$;

$R^2$, $R^3$ and $R^6$ are each independently selected from hydrogen, $C_{1-8}$ alkyl, $C_{4-8}$ cycloalkyl, $(CH_2)_{0-4}CO_2R^7$, $(CH_2)_{0-4}CON(R^{17})_2$, $(CH_2)_{0-4}COR^7$, $(CH_2)_{2-4}OR^7$, $(CH_2)_{1-4}CF_3$, $(CH_2)_{1-4}SO_2R^7$, $(CH_2)_{0-4}SO_2N(R^{17})_2$ or $(CH_2)_{1-4}CN$;

$R^7$ is selected from hydrogen, $C_{1-8}$ alkyl, $C_{3-8}$ cycloalkyl or $(CH_2)_{0-4}CF_3$;

$R^8$, $R^9$, $R^{10}$, $R^{14}$, $R^{15}$ and $R^{16}$ are each independently selected from hydrogen, $C_{1-8}$ alkyl, $C_{3-8}$ cycloalkyl, $(CH_2)_{2-4}OR^7$ or $(CH_2)_{0-4}CF_3$;

$R^{13}$ is selected from hydrogen, $C_{1-8}$ alkyl, $C_{3-8}$ cycloalkyl, $(CH_2)_{2-4}OR^7$, $OR^7$ or $(CH_2)_{0-4}CF_3$;

$R^{17}$ and $R^{18}$ are each independently selected from is selected from hydrogen, $C_{1-8}$ alkyl, $C_{3-8}$ cycloalkyl or $(CH_2)_{1-4}CF_3$;

$R^{26}$ is selected from hydrogen or $OR^{28}$;

$R^{28}$ is selected from hydrogen, $C_{1-8}$ alkl, $C_{3-8}$ cycloalkyl, $(CH_2)_{0-4}OR^7$ or $(CH_2)_{0-4}CF_3$;

each X is independently selected from halogen, cyano, nitro, $C_{1-8}$ alkyl, $C_{3-8}$ cycloalkyl, $(CH_2)_{0-4}OR^7$ or $(CH_2)_{0-4}CF_3$;

m, p and q are each independently an integer of from zero to two, provided that when q is zero, $R^{26}$ is hydrogen; and n, o, and s are each independently an integer of from zero to four;

or a pharmaceutically acceptable salt thereof.

2. The compound of claim 1 of the formula:

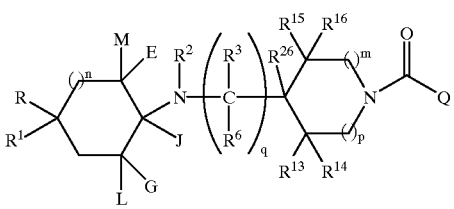

wherein $R^1$ is selected from unsubstituted, mono-, di- or tri-substituted phenyl wherein the substituents on the phenyl are independently selected from halogen, $CF_3$, cyano, nitro, $N(R^{17})_2$, $NR^{17}COR^{18}$, $NR^{17}CON(R^{18})_2$, $NR^{17}SO_2R^7$, $NR^{17}SO_2N(R^{18})_2$, $OR^7$, $(CH_2)_{0-4}CO_2R^{17}$, $(CH_2)_{0-4}CON(R^{17})_2$, $(CH_2)_{0-4}SO_2N(R^{17})_2$, $(CH_2)_{0-4}SO_2R^7$ or $C_{1-4}$ alkyl; or unsubstituted, mono-, di- or tri-substituted pyridyl, pyrazinyl, thienyl, thiazolyl, furanyl, quinazolinyl or naphthyl wherein the substituents on the pyridyl, pyrazinyl, thienyl, thiazolyl, furanyl, quinazolinyl or naphthyl are independently selected from $CF_3$, cyano, nitro, amino, $(CH_2)_{0-4}CO_2R^{17}$, $(CH_2)_{0-4}CON(R^{17})_2$, $(CH_2)_{0-4}SO_2N(R^7)_2$,$(CH_2)_{0-4}SO_2R^7$, phenyl, $OR^7$, halogen, $C_{1-4}$ alkyl or $C_{3-8}$ cycloalkyl;

R is selected from hydrogen, cyano, $OR^7$, $CO_2R^{17}$, $CON(R^{17})_2$, $SO_2R^7$, $SO_2N(R^{17})_2$, tetrazole, isooxadiazole, unsubstituted, mono- or di-substituted phenyl wherein the substituents on the phenyl are selected from halogen, cyano, nitro, $OR^7$, $(CH_2)_{0-4}CO_2R^{17}$, $(CH_2)_{0-4}CON(R^{17})_2$, $N(R^{17})_2$, $NR^{17}COR^7$, $NR^{17}CON(R^{18})_2$, $NR^{17}SO_2R^7$, $NR^{17}SO_2N(R^{18})_2$, $(CH_2)_{0-4}SO_2N(R^{17})_2$, $(CH_2)_{0-4}SO_2R^7$ or $C_{1-4}$ alkyl;

E, G, L, M and J are each independently selected from hydrogen, $C_{1-8}$ alkyl, $C_{3-8}$ cycloalkyl or $(CH_2)_{0-4}CF_3$;

$R^2$, $R^3$ and $R^6$ are each independently selected from hydrogen, $C_{1-6}$ alkyl, $C_{4-6}$ cycloalkyl, $(CH_2)_{0-4}CO_2R^7$, $(CH_2)_{0-4}CON(R^{17})_2$, $(CH_2)_{0-4}COR^7$, $(CH_2)_{2-4}OR^7$, $(CH_2)_{1-4}CF_3$,$(CH_2)_{1-4}SO_2R^7$, $(CH_2)_{0-4}SO_2N(R^{17})_2$ or $(CH_2)_{1-4}CN$;

$R^8$, $R^9$, $R^{10}$, $R^{14}$, $R^{15}$ and $R^{16}$ are each independently selected from hydrogen, $C_{1-6}$ alkyl, $C_{3-6}$ cycloalkyl, $(CH_2)_{2-4}OR^7$ or $(CH_2)_{0-4}CF_3$;

$R^{13}$ is selected from hydrogen, $C_{1-6}$ alkyl, $C_{3-6}$ cycloalkyl, $(CH_2)_{2-4}OR^7$, $OR^7$ or $(CH_2)_{0-4}CF_3$;

$R^{28}$ is selected from hydrogen, $C_{1-6}$ alkyl, $C_{3-6}$ cycloalkyl, $(CH_2)_{2-4}OR^7$ or $(CH_2)_{0-4}CF_3$;

m, n, and q are each independently an integer from zero to two, provided that when q is zero, $R^{26}$ is hydrogen; and p is an integer from zero to one;

or a pharmaceutically acceptable salt thereof.

3. The compound of claim 2, of the formula

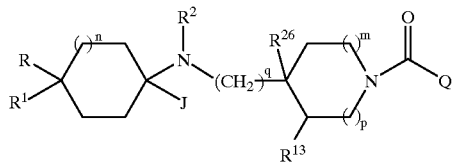

wherein Q is

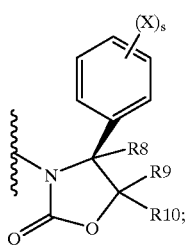

$R^2$ is selected from hydrogen, $C_{1-6}$ alkyl, $C_{4-6}$ cycloalkyl or $(CH_2)_{1-4}CF_3$;

$R^7$ is selected from hydrogen, $C_{1-6}$ alkyl, $C_{3-6}$ cycloalkyl or $(CH_2)_{0-3}CF_3$;

$R^{13}$ is hydrogen or $OR^7$;

$R^{17}$ and $R^{18}$ are each independently selected from is selected from hydrogen, $C_{1-6}$ alkyl, $C_{3-6}$ cycloalkyl or $(CH_2)_{1-4}CF_3$; and $R^{26}$ is hydrogen or $OR^{28}$, wherein $R^{28}$ is hydrogen or $C_{1-6}$ alkyl;

or a pharmaceutically acceptable salt thereof.

4. The compound of claim 3, of the formula

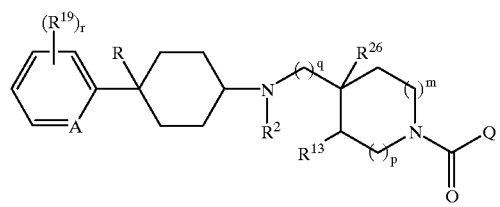

wherein A is C—$R^{19}$ or N;

R is selected from hydrogen, cyano, hydroxy, $CO_2R^{17}$, $CON(R^{17})_2$, $SO_2R^7$, $SO_2N(R^{17})_2$;

$R^2$ is selected from hydrogen or $CH_2CF_3$;

$R^{13}$ is selected from hydrogen or hydroxy;

each $R^{19}$ is independently selected from halogen, $CF_3$, cyano, nitro, amino, $OR^7$, $CO_2R^{17}$, $CON(R^{17})_2$ or $C_{1-4}$ alkyl;

$R^{26}$ is selected from hydrogen or hydroxy;

each X is halogen;

q is an integer from zero to one, provided that when q is zero, $R^{26}$ is hydrogen;

r is an integer from zero to two; and s is an integer from zero to three;

or a pharmaceutically acceptable salt thereof.

5. The compound of claim 4, selected from

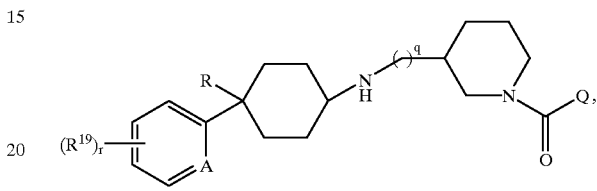

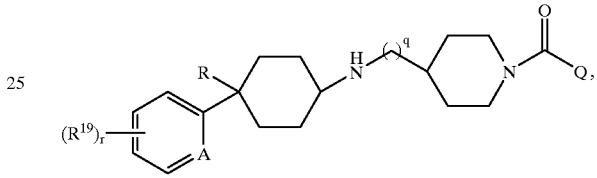

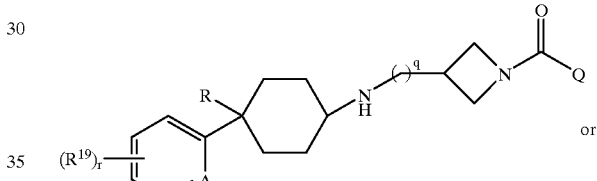

or

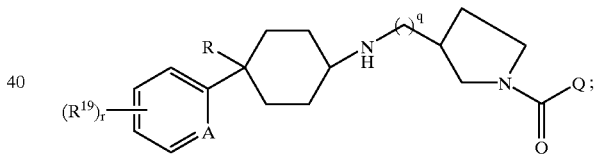

wherein Q is

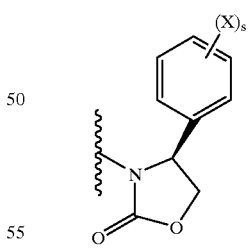

wherein R is selected from hydrogen or cyano;

$R^{19}$ is selected from hydrogen, halogen, $C_{1-6}$ alkyl or $CF_3$; and each X is fluoro;

or a pharmaceutically acceptable salt thereof.

6. The compound of claim 5, which is

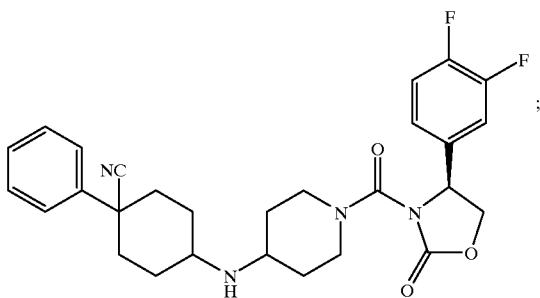

or a pharmaceutically acceptable salt thereof.

7. A pharmaceutical composition comprising a therapeutically effective amount of a compound of claim 1 and a pharmaceutically acceptable carrier.

8. A pharmaceutical composition made by combining a therapeutically effective amount of a compound of claim 1 and a pharmaceutically acceptable carrier.

9. A process for making a pharmaceutical composition comprising combining a compound of claim 1 and a pharmaceutically acceptable carrier.

10. The composition of claim 7 further comprising a testosterone 5-alpha reductase inhibitor.

11. The composition of claim 10, wherein the testosterone 5-alpha reductase inhibitor is a type 1, a type 2, both a type 1 and a type 2 or a dual type 1 and type 2 testosterone 5-alpha reductase inhibitor.

12. The composition of claim 11, wherein the testosterone 5-alpha reductase inhibitor is a type 2 testosterone 5-alpha reductase inhibitor.

13. The composition of claim 12, wherein the testosterone 5-alpha reductase inhibitor is finasteride.

14. A method of treating benign prostatic hyperplasia in a subject in need thereof which comprises administering to the subject a therapeutically effective amount of the compound of claim 1.

15. The method of claim 14, wherein the compound additionally does not cause a fall in blood pressure at dosages effective to alleviate benign prostatic hyperplasia.

16. The method of claim 15, wherein the compound is administered in combination with a testosterone 5-alpha reductase inhibitor.

17. The method of claim 16, wherein the testosterone 5-alpha reductase inhibitor is finasteride.

18. A method of treating benign prostatic hyperplasia in a subject in need thereof which comprises administering a therapeutically effective amount of the composition of claim 7.

19. The method of claim 18, wherein the composition further comprises a therapeutically effective amount of a testosterone 5-alpha reductase inhibitor.

20. A method of relaxing lower urinary tract tissue in a subject in need thereof which comprises administering to the subject a therapeutically effective amount of the compound of claim 1.

21. The method of claim 20, wherein the compound additionally does not cause a fall in blood pressure at dosages effective to relax lower urinary tract tissue.

22. The method of claim 20, wherein the compound is administered in combination with a testosterone 5-alpha reductase inhibitor.

23. The method of claim 22, wherein the testosterone 5-alpha reductase inhibitor is finasteride.

24. A method of treating a condition which is susceptible to treatment by antagonism of the alpha 1a receptor which comprises administering to a subject in need thereof an amount of the compound of claim 1 effective to treat the condition.

25. A method of eliciting an alpha 1a antagonizing effect in a mammal in need thereof, comprising administering to the mammal a therapeutically effective amount of the compound of claim 1.

* * * * *